United States Patent
Salinas et al.

(10) Patent No.: US 11,911,208 B2
(45) Date of Patent: Feb. 27, 2024

(54) SYSTEMS AND METHODS FOR THE DETECTION OF FLUID BUILD-UP RESULTING FROM AN INJURY USING ULTRASOUND IMAGING

(71) Applicant: The Government of the United States, as Represented by the Secretary of the Army, Fort Detrick, MD (US)

(72) Inventors: Jose Salinas, San Antonio, TX (US); Ronald D. Grisell, Spring Branch, TX (US); Sena R. Veazey, San Antonio, TX (US); Saul J. Vega, San Antonio, TX (US)

(73) Assignee: The Government of the United States, as Represented by the Secretary of the Army, Fort Detrick, MD (US)

( * ) Notice: Subject to any disclaimer, the term of this patent is extended or adjusted under 35 U.S.C. 154(b) by 229 days.

(21) Appl. No.: 17/269,739

(22) PCT Filed: Aug. 21, 2019

(86) PCT No.: PCT/US2019/047462
§ 371 (c)(1),
(2) Date: Feb. 19, 2021

(87) PCT Pub. No.: WO2020/068306
PCT Pub. Date: Apr. 2, 2020

(65) Prior Publication Data
US 2021/0196227 A1    Jul. 1, 2021

Related U.S. Application Data

(60) Provisional application No. 62/720,262, filed on Aug. 21, 2018.

(51) Int. Cl.
  A61B 8/06    (2006.01)
  A61B 8/00    (2006.01)
  B06B 1/06    (2006.01)

(52) U.S. Cl.
  CPC ............ *A61B 8/06* (2013.01); *A61B 8/465* (2013.01); *A61B 8/469* (2013.01); *B06B 1/0607* (2013.01); *B06B 2201/76* (2013.01)

(58) Field of Classification Search
  CPC .......... A61B 8/06; A61B 8/465; A61B 8/469; A61B 8/08; A61B 8/0858; A61B 8/0891;
  (Continued)

(56) References Cited

U.S. PATENT DOCUMENTS 5,987,094 A    11/1999    Clarke et al.
6,650,924 B2   11/2003    Kuth et al.
(Continued)

FOREIGN PATENT DOCUMENTS

WO    98/58588 A1    12/1998
WO    2007/025218 A2    3/2007
(Continued)

OTHER PUBLICATIONS

Calvert, N., et al., "Ultrasound for Central Venous Cannulation: Economic Evaluation of Cost-Effectiveness," Anesthesia, vol. 59, Issue 11, pp. 1116-1120, Nov. 2004.
(Continued)

*Primary Examiner* — Joel Lamprecht
*Assistant Examiner* — Nyrobi Celestine
(74) *Attorney, Agent, or Firm* — Leigh Z. Callander

(57) ABSTRACT

Improved systems and methods for diagnosing an injury of a patient. The system and methods provide for more accurate scans of the injury thereby enabling a combat medic, a medical technician, or even untrained individuals to quickly diagnose the injury. By providing more accurate informa-
(Continued)

tion, the systems and methods provide the technician with additional information regarding treatment options, such as whether to transport the patient or treat the patient in place, potential for aspiration, and other information about dangerous fluid build-up such as size, depth, and types of surrounding tissues, thereby increasing survivability of the patient. The systems and methods can also provide a diagnosis of the injury as well as suggestions on actions to take to treat the patient.

18 Claims, 16 Drawing Sheets

(58) Field of Classification Search
CPC ....... A61B 8/461; A61B 8/488; A61B 8/5207; A61B 8/5223; A61B 8/145; B06B 1/0607; B06B 2201/76
See application file for complete search history.

(56) References Cited

U.S. PATENT DOCUMENTS

| | | | |
|---|---|---|---|
| 7,920,731 | B2 | 4/2011 | Moreau-Gobard |
| 8,394,031 | B2 | 3/2013 | Mansy et al. |
| 10,217,213 | B2 | 2/2019 | Blackbourne et al. |
| 2005/0004466 | A1* | 1/2005 | Hynynen ............ G01S 15/8977 600/449 |
| 2005/0020918 | A1 | 1/2005 | Wilk et al. |
| 2007/0066895 | A1 | 3/2007 | Sikdar et al. |
| 2008/0077011 | A1 | 3/2008 | Azuma et al. |
| 2008/0183077 | A1 | 7/2008 | Moreau-Gobard et al. |
| 2008/0234567 | A1 | 9/2008 | Tearney et al. |
| 2009/0149748 | A1 | 6/2009 | Lenhardt et al. |
| 2009/0177092 | A1 | 7/2009 | Riechers et al. |
| 2010/0222663 | A1 | 9/2010 | Wilder et al. |
| 2010/0274130 | A1 | 10/2010 | Anand et al. |
| 2012/0016240 | A1 | 1/2012 | Lee et al. |
| 2012/0289827 | A1* | 11/2012 | Ismail ................ A61B 5/0035 600/430 |
| 2013/0018240 | A1 | 1/2013 | McCoy |
| 2013/0197370 | A1 | 8/2013 | Burlina et al. |
| 2014/0213901 | A1 | 7/2014 | Shackelford |
| 2014/0316267 | A1* | 10/2014 | Barry ................. A61B 8/4444 600/438 |
| 2015/0148675 | A1 | 5/2015 | Haupt |
| 2016/0239959 | A1* | 8/2016 | Blackbourne .......... G06V 10/40 |
| 2017/0258445 | A1* | 9/2017 | Van Alphen ......... A61B 8/4472 |
| 2017/0360412 | A1* | 12/2017 | Rothberg ............ G06T 11/60 |

FOREIGN PATENT DOCUMENTS

| | | |
|---|---|---|
| WO | 2008/073560 A2 | 6/2008 |
| WO | 2008/073560 A3 | 6/2008 |

OTHER PUBLICATIONS

Chan, Stweart Siu Wa, et al., "Emergency Bedside Ultrasound to Detect Pneumothorax," Academic Emergency Medicine, vol. 10, No. 1, pp. 91-94, Jan. 2003.

Gayzik, F.S., Moreno, D.P., Danelson, K.A. et al. External Landmark, Body Surface, and Volume Data of a Mid-Sized Male in Seated and Standing Postures. Ann Biomed Eng 40, 2019, Abstract (2012). https://doi.org/10.1007/s10439-012-0546-z.

Gu, Wan-Jie, et al., "Efficacy of Ultrasound-Guided Radial Artery Catheterization: A Systematic Review and Meta-Analysis of Randomized Controlled Trials," Critical Care, vol. 18, Article R93, Mar. 8, 2014.

Hayes, Ashley R., et al., "Comparison of Organ Location, Morphology, and Rib Coverage of a Midsized Male in the Supine and Seated Positions." Computational and Mathematical Methods in Medicine, vol. 2013, Article ID 419821, 12 pages, Feb. 2013.

Kline, Jonathan P., et al., "Detection of Pneumothorax with Ultrasound," AANA Journal, vol. 81, No. 4, pp. 265-271, Aug. 2013.

Lichtenstein, Daniel A., et al., "Ultrasound Diagnosis of Occult Pneumothorax," Critical Care Medicine, vol. 33, No. 6, pp. 1231-1238, 2005.

Perera, Phillips, et al., "The RUSH Exam: Rapid Ultrasound in Shock in the Evaluation of the Critically Ill," Emeg Med Clin N Am, vol. 28, pp. 29-56, 2010.

Soldati, Gino, et al., "The Ultrasonographic Deep Sulcus Sign in Traumatic Pneumothorax," Ultrasound in Medicine and Biology, vol. 32, No. 8, pp. 1157-1163, 2006.

Testa, A., et al., "Psychiatric Emergencies (Part III): Psychiatric Symptoms Resulting from Organic Diseases," European Review for Medical and Pharmacological Sciences, vol. 17, Suppl 1, pp. 86-99, Feb. 2013.

Tsai, C-L, et al., "Ring Down Artefacts on Abdominal Sonography to Predict Pulmonary Abnormalities in the Emergency Department." Emergency Medical Journal, vol. 22, pp. 747-748, 2005.

Ueda, K., et al., "Ultrasound Visual Image-Guided vs Doppler Auditory-Assisted Radial Artery Cannulation in Infants and Small Children by Non-expert Anaesthesiologists: A Randomized Prospective Study," British Journal of Anaesthesia, vol. 110, Issue 2, pp. 281-286, Feb. 2013.

U.S. Patent and Trademark Office, International Search Report for PCT Application No. PCT/US2019/047462, dated Mar. 10, 2020, pp. 3-4.

U.S. Patent and Trademark Office, Written Opinion for PCT Application No. PCT/US2019/047462, Mar. 10, 2020, dated pp. 4-8.

* cited by examiner

SYSTEMS AND METHODS FOR THE DETECTION OF FLUID BUILD-UP RESULTING FROM AN INJURY USING ULTRASOUND IMAGING

This patent application is a national stage application from PCT international application number PCT/US2019/047462, filed on Aug. 21, 2019 and which claims the benefit of U.S. Patent Application Ser. No. 62/720,262 filed on Aug. 21, 2018, the entirety of both has herein incorporated by reference.

This invention was made with government support under Contract Number W81XWH-11-D-0027 awarded by the Department of the Army. The U.S. Government has certain rights in the invention.

BACKGROUND

When diagnosing an injured person suffering from one or more injuries, it is important to be able to ascertain the location, type and extent of the injury as soon as possible. For example, hemorrhages can be very small and difficult to detect. However, it is also important that the diagnosis be accurate so appropriate treatment advice can be provided to increase the survivability of the injured person until he or she can be evacuated to a treatment center. This is especially critical for soldiers injured on the battlefield.

Fluoroscopy is an imaging technique that uses X-rays to obtain real-time moving images of the interior of an object. This technique has been applied in the past to image injuries but has proven ineffective due to the bulky size of fluoroscopes. Also, this type of imaging is not able to accurately detect hemorrhages of a small size. Further, the ability to accurately detect small hemorrhages remains an issue with standard Focused Assessment with Sonography in Trauma (FAST) examinations that are typically performed for trauma victims.

SUMMARY OF THE INVENTION

The invention described herein is directed to improved systems and methods for diagnosing an injury of a patient (i.e. human or animal). The systems are compact and can therefore be easily employed on the battlefield in combat situations or at the scene of an accident and can be used to treat multiple victims within a short period of time. They also provide for more accurate scans of the injury thereby enabling a combat medic, a medical technician, or even untrained individuals to quickly diagnose the injury thereby helping to extend the life of the patient until full treatment can be provided. The systems can be used to supplement existing FAST examinations thereby enhancing the results of these examinations. Further, by providing more accurate information, the systems provide the technician with information regarding whether to transport the patient or treat the patient in place thereby increasing survivability of the patient. The systems can also provide a diagnosis of the injury as well as suggestions on actions to take to treat the patient. Thus, for example, in combat situations, events which can cause hemorrhages, such as explosions, shrapnel, bullets and glass, can be effectively managed to lower the risk of a soldier dying from internal bleeding or hemorrhagic shock.

In an exemplary implementation, a method for diagnosing an injury, includes applying, from an ultrasound device, a first beam to an area of an injury and applying, from the ultrasound device, a second beam to the area of the injury. The method further includes generating, via processing circuitry and based on signals from the second beam, image data of the area of the injury, and processing, via the processing circuitry, the image data and providing a diagnosis of the injury based on the processing. The method also includes generating an alert when the diagnosis identifies an abnormality at the area of the injury.

In at least one embodiment, the first beam is applied via a first transducer probe of the ultrasound device, and the second beam is applied via a second transducer probe of the ultrasound device. In accordance with the preceding embodiment, the first transducer probe is applied approximately orthogonally to the area of the injury, and the second transducer probe is applied at a predetermined angle of separation from the first transducer probe such that the first and second beam intersect at the area of the injury. In accordance with the preceding embodiment, the predetermined angle of separation is calculated as the arctangent of T/D1, where D1=the depth of tissue below a skin surface at the area of the injury, and T=a lateral separation distance between the first and second transducer probe. In accordance with any of the preceding embodiments, the abnormality includes at least one of internal bleeding, hemothorax, pneumothorax, edema, exudate, or pericardial effusion. In accordance with any of the preceding embodiments, at least one of the first or second beam is one of a pulsatile beam, a pulsatile constant frequency, or frequency over a range. In accordance with any of the preceding embodiments, the processing of the image data includes comparing one or more frames of the image data to a predetermined threshold, and the providing of the diagnosis and generating of the alert are based on the comparing. In accordance with the preceding embodiments, the predetermined threshold is determined based on predetermined anatomy data of patients having the injury. In accordance with any of the preceding embodiments, the diagnosis is determined as a function of anatomy data of a patient having the injury. In accordance with the fourth embodiment, the depth of tissue is based on a location of the injury and anatomy data of a patient having the injury. In accordance with any of the preceding embodiments, the diagnosis includes information indicating treatment options for the injury. In accordance with any of the preceding embodiments, the alert includes a probability indicator indicating the probability of internal injury based on the processing of the image data In an exemplary implementation, a system for diagnosing an injury, includes an ultrasound device configured to apply a first beam to an area of an injury, and apply a second beam to the area of the injury. The system also includes processing circuitry configured to generate, based on signals from the second beam, image data of the area of the injury, process the image data, and provide a diagnosis of the injury based on the processing. The processing circuitry is further configured to generate an alert when the diagnosis identifies an abnormality at the area of the injury.

In at least one embodiment, the ultrasound devices include a first transducer probe configured to apply the first beam, and a second transducer probe configured to apply the second beam. In accordance with the preceding embodiment, the first transducer probe is applied approximately orthogonally to the area of the injury, and the second transducer probe is applied at a predetermined angle of separation from the first transducer probe such that the first and second beam intersect at the area of the injury. In accordance with the preceding embodiment, the predetermined angle of separation is calculated as the arctangent of T/D1 where D1=the depth of tissue below a skin surface at the area of the injury, and T=a lateral separation distance between the first and second transducer probe. In accordance with any of the preceding embodiments, the abnormality includes at least one of internal bleeding, hemothorax, pneumothorax, edema, exudate, or pericardial effusion. In accordance with any of the preceding embodiments, the first beam is one of a pulsatile beam, a pulsatile constant frequency, or frequency over a range. In accordance with any of the preceding embodiments, the processing circuitry is configured to process the image data by comparing one or more frames of the image data to a predetermined threshold, and the providing of the diagnosis and generating of the alert are based on the comparing. In accordance with the preceding embodiment, the predetermined threshold is determined based on predetermined anatomy data of patients having the injury. In accordance with any of the preceding embodiments, the diagnosis is determined as a function of anatomy data of a patient having the injury. In accordance with the fourth embodiment, the depth of tissue is based on a location of the injury and anatomy data of a patient having the injury. In accordance with any of the preceding embodiments, the diagnosis includes information indicating treatment options for the injury. In accordance with any of the preceding embodiments, the alert includes a probability indicator indicating the probability of internal injury based on the processing of the image data In an exemplary implementation, a method for diagnosing an injury, includes applying, from vibration device, a vibration to an area near an injury and applying, from an ultrasound device, a beam to the area of the injury. The method further includes generating, via processing circuitry of the ultrasound device and based on signals from the beam, image data of the area of the injury, processing, via the processing circuitry, the image data and providing a diagnosis of the injury based on the processing. The method also includes generating an alert when the diagnosis identifies an abnormality at the area of the injury.

In at least one embodiment according to the method in the previous paragraph, the abnormality includes at least one of internal bleeding, hemothorax, pneumothorax, edema, exudate, or pericardial effusion. In accordance with the preceding embodiment, wherein a vibration frequency output by the vibration device is adjusted as a function of the image data. In accordance with the preceding embodiment, a transducer probe of the ultrasound device applies the beam approximately orthogonally to the area of the injury, and the vibration device is applied on the skin at a lateral distance D from the area of the injury. In accordance with the preceding embodiment, the distance D is lateral distance which prevents interference generated by the vibration device. In accordance with any of the preceding embodiments within this paragraph, the vibration emitted by the vibration device is a pulsatile constant frequency or frequency over a range. In accordance with any of the preceding embodiments within this paragraph, the processing of the image data includes comparing one or more frames of the image data to one or more predetermined patterns, and the providing of the diagnosis and generating of the alert are based on the comparing. In accordance with any of the preceding embodiments within this paragraph, the diagnosis is determined as a function of predetermined anatomy data of patients having the injury. In accordance with any of the preceding embodiments within this paragraph, the diagnosis includes information indicating treatment options for the injury. In accordance with any of the preceding embodiments within this paragraph, the alert includes a probability indicator indicating the probability of internal injury based on the processing of the image data In an exemplary implementation, a system for diagnosing an injury, includes: a vibration device configured to apply a vibration to an area near an injury and an ultrasound device configured to apply a beam to the area of the injury. The system further includes processing circuitry configured to generate, based on signals from the beam, image data of the area of the injury, process the image data, and provide a diagnosis of the injury based on the processing. The processing circuitry is further configured to generate an alert when the diagnosis identifies an abnormality at the area of the injury.

In at least one embodiment of the system of the previous paragraph, the abnormality includes at least one of internal bleeding, hemothorax, pneumothorax, edema, exudate, or pericardial effusion. In accordance with the preceding embodiment, a vibration frequency output by the vibration device is adjusted as a function of the image data. In accordance with the preceding embodiment, a transducer probe of the ultrasound device applies the beam orthogonally to the area of the injury, and the vibration device is applied on the skin at a lateral distance D from the area of the injury. In accordance with the preceding embodiment, the distance D is a lateral distance which prevents interference generated by the vibration device. In accordance with any of the preceding embodiments, the vibration emitted by the vibration device is a pulsatile constant frequency or frequency over a range. In accordance with any of the preceding embodiments within this paragraph, the processing of the image data includes comparing one or more frames of the image data to one or more predetermined patterns, and the providing of the diagnosis and generating of the alert are based on the comparing. In accordance with any of the preceding embodiments within this paragraph, the diagnosis is determined as a function of predetermined anatomy data of patients having the injury. In accordance with any of the preceding embodiments within this paragraph, the diagnosis includes information indicating treatment options for the injury. In accordance with any of the preceding embodiments within this paragraph, the alert includes a probability indicator indicating the probability of internal injury based on the processing of the image data.

The foregoing paragraphs have been provided by way of general introduction and are not intended to limit the scope of the following claims. Therefore, the above summary is not intended to be an exhaustive discussion of all the features or embodiments of the present disclosure. A more detailed description of the features and embodiments of the present disclosure will be described in the detailed description section.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
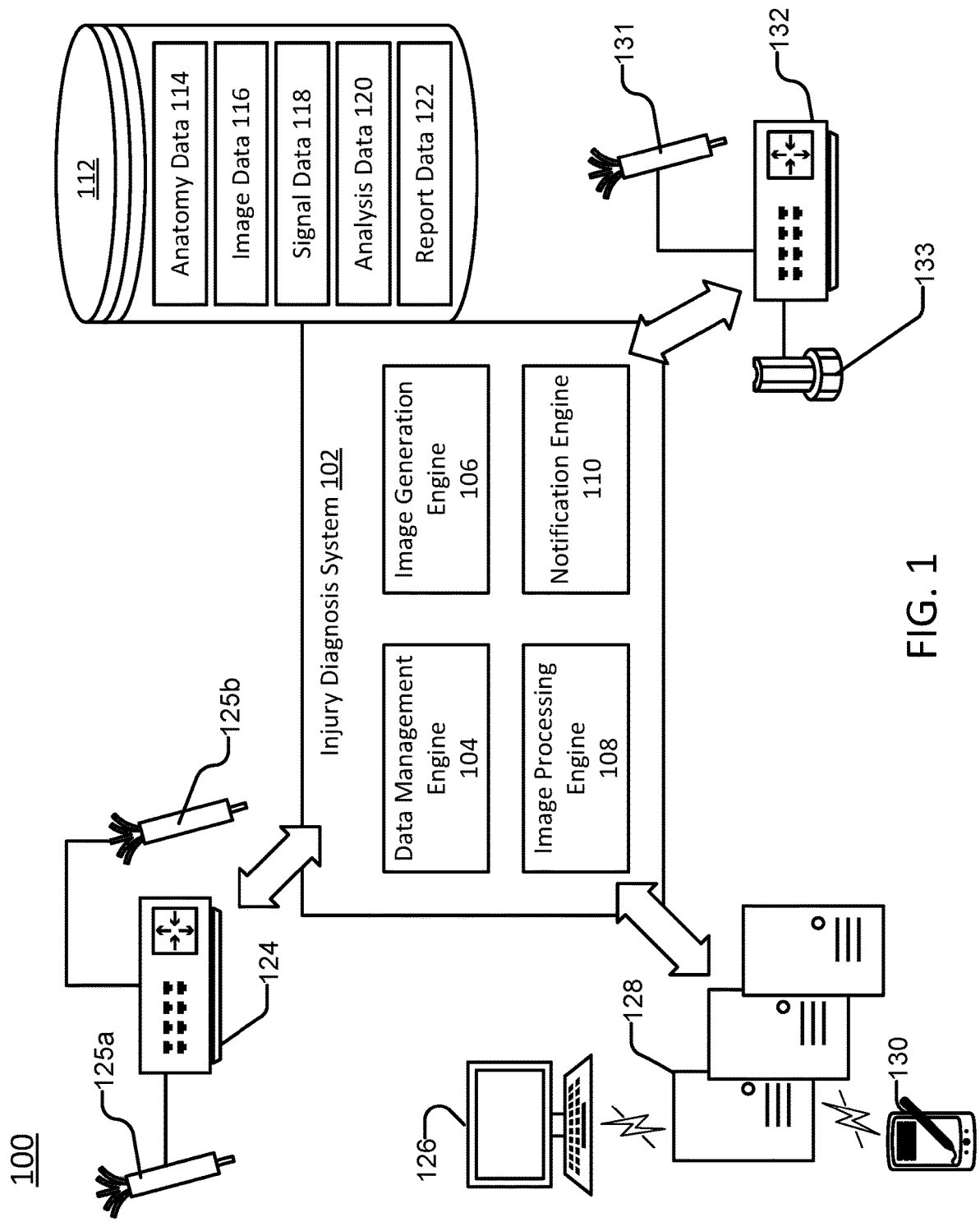
FIG. 1 is a diagram of an environment for an injury diagnosis system according to one example.

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

In the detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

It will be appreciated that as used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

It will be appreciated that as used herein, the term "abnormality," as detected by the system and unless specifically described, can be used to describe internal injuries such as bleeding, pools of fluid, air pockets, hemothorax, pneumothorax, edema, exudate, and/or pericardial effusion.

It will also be appreciated that as used herein, any reference to a range of values is intended to encompass every value within that range, including the endpoints of said ranges, unless expressly stated to the contrary.

As described further herein, aspects of the present invention are described below with reference to flowchart illustrations and/or block diagrams of methods, apparatus (systems) and non-transitory computer-readable mediums according to embodiments of the invention. It will be understood that one or more blocks of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, an operating system, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, a processor, other programmable data processing apparatus, or other devices to cause a series of operational steps to be performed on the computer, the processor, or other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises at least one executable instruction for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to the drawings, wherein like reference numerals designate identical or corresponding parts throughout the several views, the following description relates to a dedicated system and method for finding activities that suits personal preference and schedule of a user and for managing activities that the user signed up for participation.

FIG. 1 is a diagram of an example environment 100 for an injury diagnosis system 102 according to one example. The diagram illustrates a series of interactions between one or more devices in the injury diagnosis system 102 which is configured to diagnose injuries of an injured subject. For example, the injury diagnosis system 102 can be used to detect the location of an injury and to generate diagnosis information regarding the extent of the injury as well as treatment options. The injury diagnosis system 102 can be employed by medical and non-medical technicians both on and off the battlefield to rapidly identify hemorrhages of injured individuals and to determine on-site treatment options or requests for evacuation.

The injury diagnosis system 102 can include a variety of interconnected equipment connected either directly or via a network which provide data for determining the diagnosis of an injury. For example, an ultrasound device 124 having one or more attached transducer probes 125 can be used to send and receive sounds waves via the piezoelectric effect. Specifically, in the transducer probe(s) 125, there can be one or more quartz piezoelectric crystals that change shape rapidly when an electric current is applied to them. The rapid shape changes, or vibrations, of the crystals produce sound waves that travel outward. Conversely, when sound or pressure waves hit the crystals, they emit electrical currents that can be converted into digital readings. Therefore, the same crystals can be used to send and receive sound waves. The transducer probes 125 also have a sound absorbing substance to eliminate back reflections from the probe itself and an acoustic lens to help focus the emitted sound waves. The electric current applied to crystals to generate sound waves is controlled by a central processing unit (CPU) of the ultrasound device 124 or other connected computing hardware. As such, the CPU sends electrical currents to the transducer probe to emit sound waves. The CPU also receives the electrical pulses from the probes that were created from the returning echoes and generates digital data based on a conversion of these electrical pulse readings. Thus, the CPU can perform all of the calculations involved in processing signals received by a transducer probe 125. Once the raw signal data 118 are processed, the CPU generates image data 116 which can be stored on the ultrasound device 124 and displayed on a monitor that is part of the ultrasound device 124 and/or connected separately. The CPU can also store the image data 116 on a disk or transmit it to the injury diagnosis system 102 to be stored in a database 112 by a data management engine 104. Also, in one example, the ultrasound device(s) 124 and injury diagnosis system 102 can be part of the same device.

In one example, the ultrasound device 124 has at least two transducer probes 125a, 125b which are used by the injury diagnosis system 102 to diagnose an injury. A first transducer probe 125a can be used to emit a low frequency beam that causes any fluid within the tissue of an injured patient to vibrate at a greater amplitude than relatively homogeneous tissue in proportion to differences in acoustic refractive index across the interface. This results in a force on the tissue interface in proportion to such refractive differences such that the movement of the interface relative to the surrounding tissue can be imaged by a second transducer probe 125b in color or a power Doppler mode (i.e. 2D or 3D). In other words, a beam applied to solid tissue will not cause much vibration as compared to a beam applied to liquids. In one example, the second transducer probe 125b is operated at at least five times the frequency of the beam emitted by the first transducer probe 125a. This provides for less interference and sidebands thereby enhancing imaging results arising out of image processing of the signal data 118 received by the second transducer probe 125b.

The signal data 118 received by the second transducer probe 125b are received and processed by the CPU of the ultrasound device 124 and/or can be transmitted to processing circuitry of the injury diagnosis system 102 for processing to generate a plurality of sequenced image data 116. For example, in the color Doppler mode, the measurements of the signals received by the second transducer probe 125b are converted into an array of colors to show the speed and direction of the various movements of tissue interfaces and their nearby tissues or fluids (if any). The power Doppler mode is similar but provides greater detail of the blood flow while balancing this enhancement against the inability to indicate a direction of the blood flow. These images are time-sliced and then processed by the CPU of the ultrasound device 124 and/or the processing circuitry of the injury diagnosis system 102 to generate a time-sequence video of blood flow and tissue movement especially near their interface as image data 116. The time-sequence, either as a whole, and/or on a frame-by-frame basis, is then analyzed by an image processing engine 108 to diagnose the extent of an injury. For example, in one implementation in color mode, the mean velocity within a pixel-divided region is determined based on a frame-by-frame comparison. The mean-velocity is then converted into a color, such as blue, when blood is flowing toward the transducer probe and red when blood is flowing away from the transducer probe. These colors are then shown on the display of the ultrasound device 124 and/or the system 102 and/or remote device 126/130 to illustrate the blood flow and tissue movements and to highlight a potential area of injury.

In one example, once the first transducer probe 125a beam has vibrated any blood and nearby tissue of the patient, the signals received by the second transducer probe 125b are then received by the injury diagnosis system 102 either via direct connection to the ultrasound device 124 or wirelessly through a network. The injury diagnosis system 102 can also receive the image data 116 generated by the ultrasound device 124 or can in some implementations receive signal data 118 of the transducer probe and generate the image data 116 internally via an image generation engine 106. When in a segmented system implementation, image generation at a remote injury diagnosis system 102 allows the ultrasound device to require less computational equipment thereby reducing the size and footprint of the ultrasound device. This can help soldiers or trauma technicians by having a more compact device that can be easily deployed. Once the image data 116 and/or signal data 118 are either received and/or the image data 116 is generated by the injury diagnosis system 102, the data are stored in a database 112 by the data management engine 104. The data management engine 104 is responsible for handling incoming, outgoing and internal data controlled by the injury diagnosis system 102. Accordingly, the data management engine 104 passes the signal data 118 received by the ultrasound device 124 to the image generation engine 106 for processing and provides the generated image data 116 to the image processing engine 108 for processing while also managing the storing and retrieval of processed data.

The image processing engine 108 processes the image data 116 received by the ultrasound 124 and/or generated by the image generation engine 106 to diagnose an injury of a patient. To do this, the image processing engine 108 segments the image data 116 on a frame-by-frame basis to identify areas of color or specific blood flow identified by the Doppler mode to determine whether there are pools of blood indicating conditions such as hemorrhaging. For example, blood between two organs, such as the kidney and liver, would result in both the liver and kidney surfaces being highlighted in Doppler mode. If there is no blood, these organs will be pressed together and there will be a much lower difference in impedance at the interface as detected by the ultrasound device 124 via the second transducer probe 125b. The amount of flow detected by Doppler can be compared by the image processing engine 108 to a predetermined threshold to determine whether the flow constitutes a blood pool indicating a hemorrhage or other injury. The amount of pooled blood and results of the comparison data generated by the image processing engine 108 are stored as analysis data 120 in the database 112 by the data management engine 104. The analysis data 120 is then processed by a notification engine 110 to generate report data 122.

The notification engine 110 of the injury diagnosis system 102 generates and stores report data 122 and presents this to the technician via a display screen of the injury diagnosis system 102, on a remote computing device 126 and/or on a screen of the ultrasound device 124/132. The report data 122 can provide time-linked images as a video or specific time-sliced images specific to the analyzed area of the patient and including color halos generated by Doppler, a probability prediction of how likely it is that the patient is suffering from internal abnormalities, such as bleeding via a hemorrhage, and diagnosis and alert information regarding the lethality of the injury and potential actions that the technician can take based on the diagnosis. These actions can include on-site surgical treatments and instructions specific to the diagnosis or instructions that the patient should be moved immediately and an indication of the closest medical facility for treatment. In one example, anatomy data 114 of the patient, such as a soldier, can be pre-stored in the database 112 or the injury diagnosis system 102 can retrieve and store anatomy data 114 from one or more devices worn by the patient or remote devices 126-130. The anatomy data 114 can include information specific to the individual such as pre-existing conditions, prior surgeries, medical conditions, allergies and other information as would be useful for the image processing engine 108 to generate analysis data 120 and notification engine 110 to generate a diagnosis and course of action in the report data 122 specific to the patient. The anatomy data 114 can also include body data following the format and structure of widely accepted body types and shapes as modeled by the Global Human Body Models Consortium (GHBMC). Alternatively, or in addition to a computer-generated report, the technician themselves can review the image data 116 and report data 122 to provide an assessment of the injury of the patient. However, this is not always easy especially in a battlefield situation so the computer-generated report including diagnosis and treatment options can save time while also providing life-saving treatment options thereby greatly increasing survivability of the injured soldier.

FIG. 1. also illustrates a second ultrasound device 132 having a transducer probe 131 and a vibration device 133. The vibration device 133 is used to create a to-and-fro sloshing movement of fluid in surrounding organs when the vibration device 133 is applied to an area at or near the injury. The vibration device 133 can be any type of device as would be understood by one of ordinary skill in the art for generating vibrations such as Parallax vibration motors and/or a TheraSpa® percussion massagers. Once the vibration device 133 is applied at or near the point of injury, it causes shifts in fluid more so than in tissue which is then picked up as Doppler frequency shifts by the transducer probe 131. These signals received by the transducer probe 131 are then processed by the CPU of the ultrasound device 132 and/or by the injury diagnosis system 102 as described previously herein with respect to the ultrasound device 124 to diagnose the injury.

Ultrasound device 124 and ultrasound device 132 are not mutually exclusive in terms of the diagnosis of an injury by the system 102 and can therefore both be used to diagnose an injury. This can be done either independently or simultaneously wherein the image processing engine 108 can compare analysis data 120 based on image data 116 from each ultrasound device to identify outliers and averages thereby providing a more accurate assessment as to the location and type of injury. This allows the system 102 to provide more a more precise diagnosis as well as enhanced treatment suggestions via combined report data 122.

One or more computing devices 126, one or more servers 128 and one or more mobile devices 130 can also be connected to the injury diagnosis system 102 either directly or via a network. The computing devices 126 and/or mobile devices 130 can be used to remotely receive and review image data 116, analysis data 120 and report data 122 transmitted by the data management engine 104. Accordingly, remote technicians can review data that is being provided by the injury diagnosis system 102 in real-time to allow remote medical experts to provide additional support for the injured patient. For example, a soldier on the battlefield with no medical expertise could receive instruction from remote medical experts on treating the injured soldier. The one or more servers 128 can also help provide for additional processing of the signal data 118 and image data 116 and can further act to push software and firmware updates as well as updated anatomy data 114 to the injury diagnosis system 102.

Figure 2:
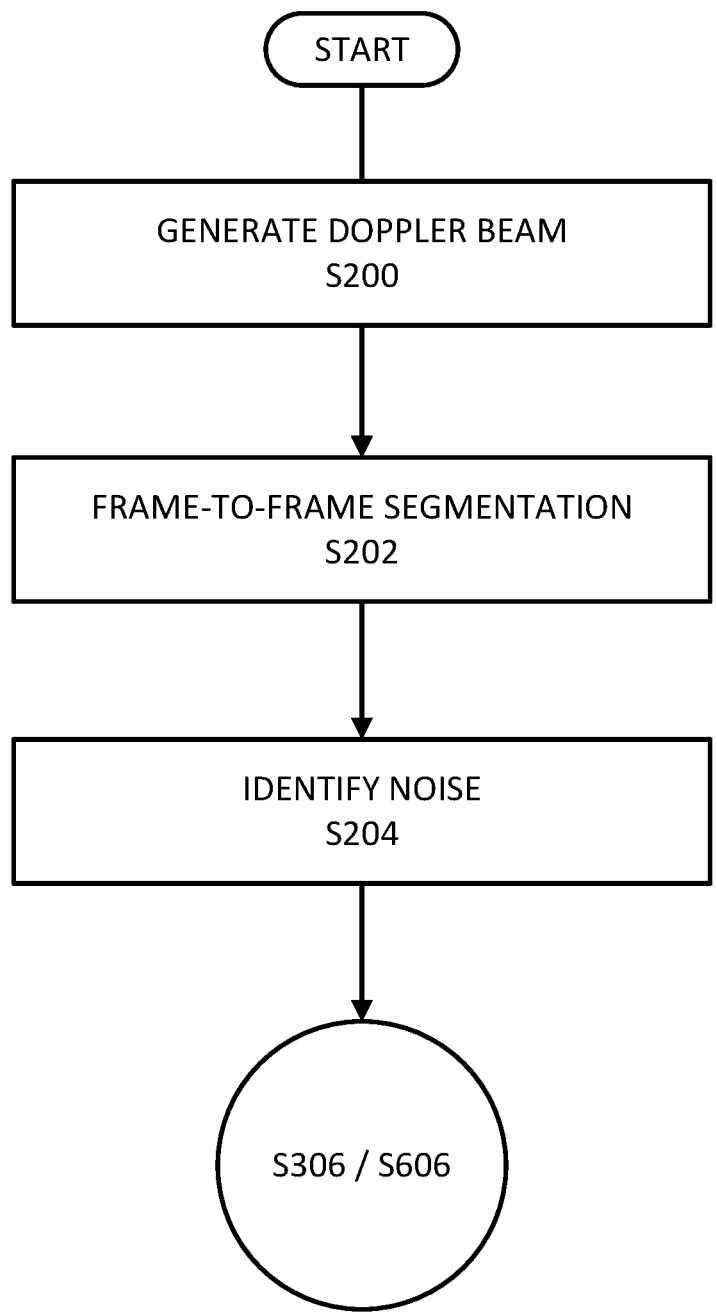
FIG. 2 is a flowchart of a noise identification process for identifying noise levels according to one example.

FIG. 2 is a flowchart of a noise identification process according to one example. As described herein, the transducer probe 125b and/or the transducer probe 131 generates a Doppler beam to be applied at or near an area of the injury of a patient at step S200. The ultrasound device 124 and/or 132 then receives the signal data 118 returned from the application of the Doppler beam and process them internally by the CPU or at the injury diagnosis system 102. This includes performing a frame-to-frame segmentation of the generated images at step S202 to identify the results of the Doppler mode for each time slice of the reading on the patient. The noise level introduced by the ultrasound device itself is then identified at step S204. For example, when performing an ultrasound, speckle noise often arises from random interference between coherent returns issued from scatters present on the surface. This degrades the quality of images and thereby reduces the ability of discrimination of details during diagnostic examination. Further noise can be created by the ambient environment as well as by movement of the patient that creates large areas of Doppler blue and red due to movement of fluids caused by the drastic movement of the patient. Accordingly, sources of the noise are identified for use during image processing by the CPU of the ultrasound device and/or the image generation engine 106 after being transmitted thereto. This information is then used during the processing of the image data 116 at step S306 of FIG. 3 and step S606 of FIG. 6 to increase the accuracy of the readings. The identification of noise levels can be done concurrently or non-concurrently with steps S302-S304 and S602-S604.

Figure 3:
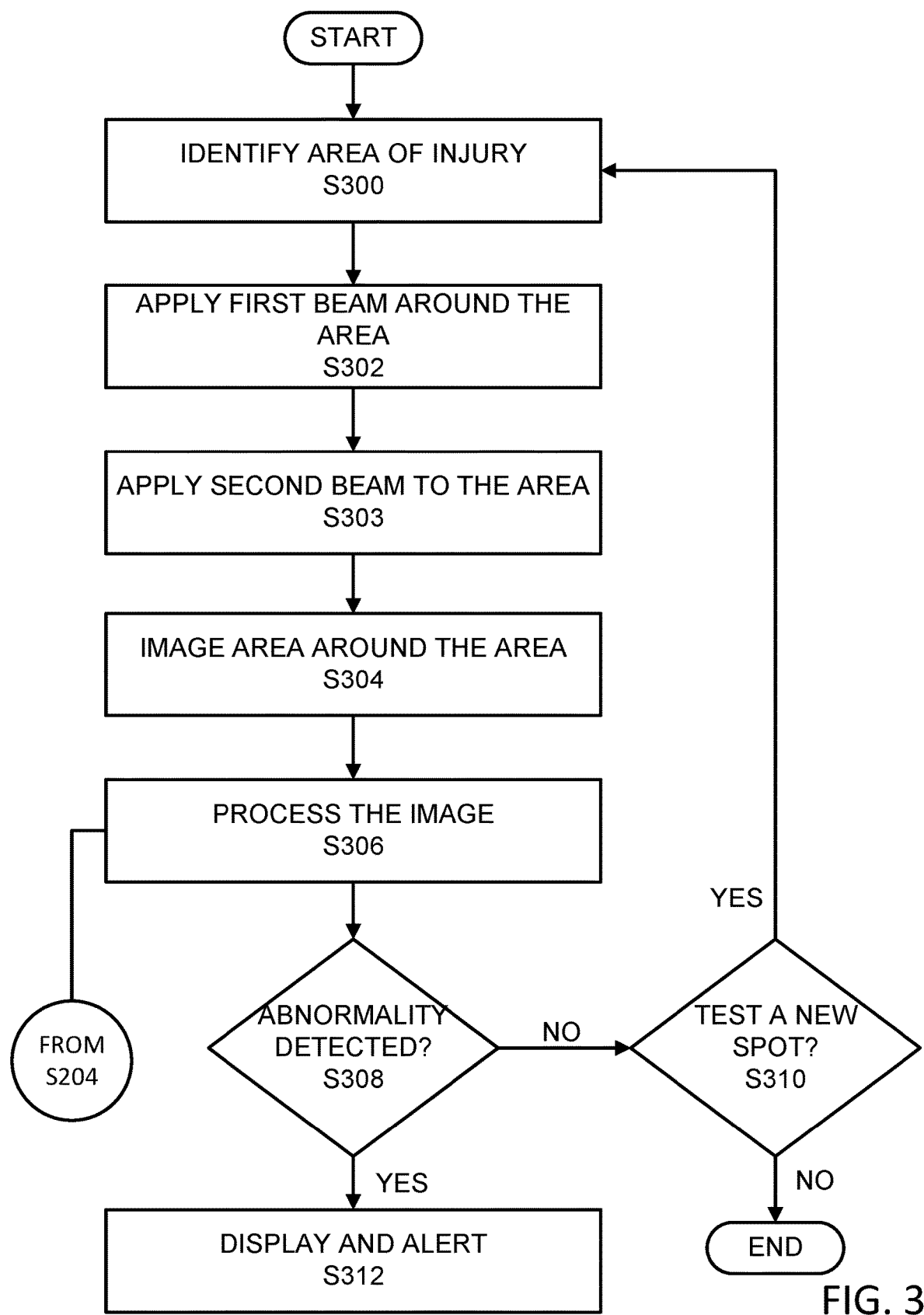
FIG. 3 is a flowchart of a diagnosis process according to one example.
Figure 4:
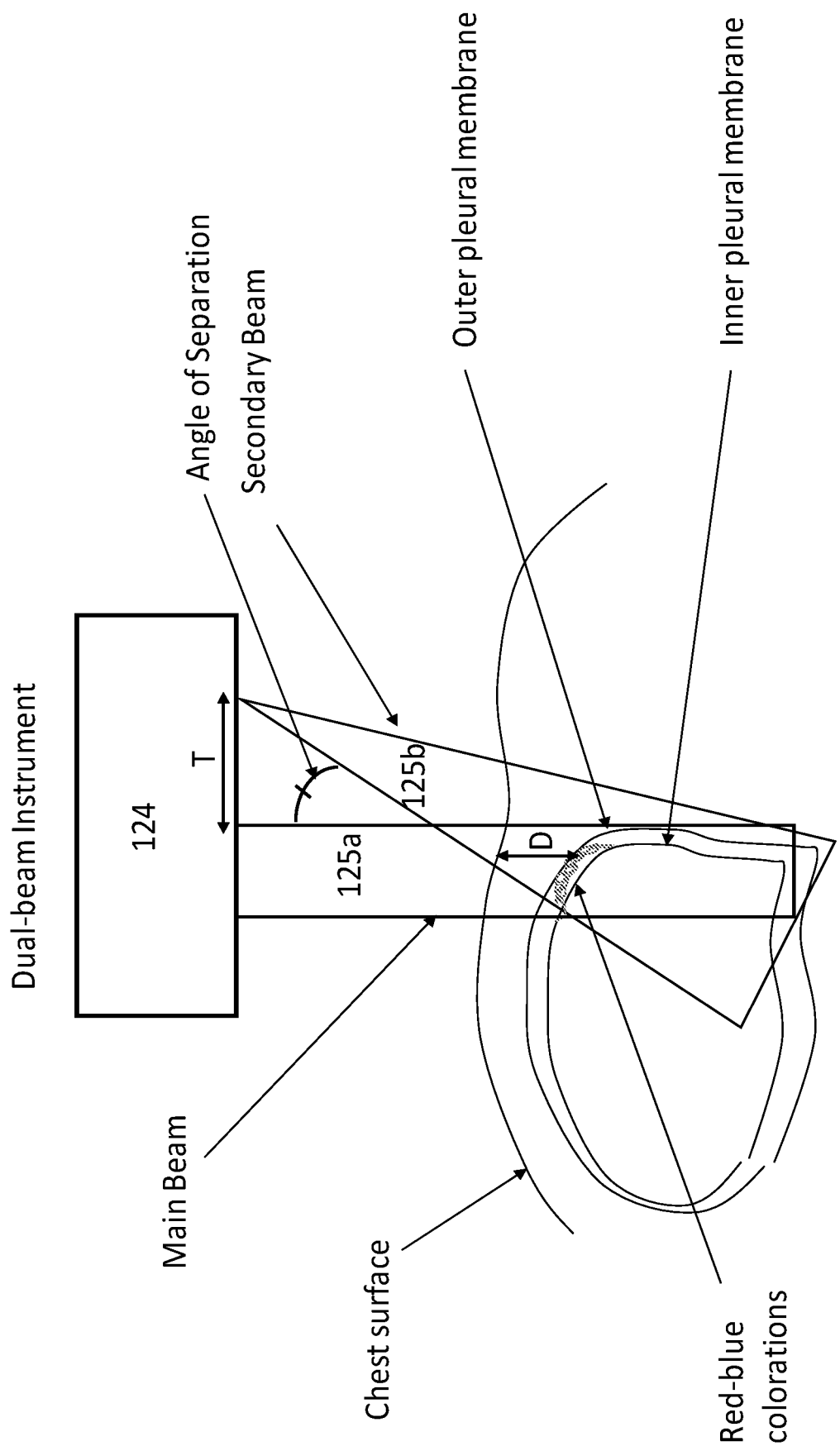
FIG. 4 is an application illustration of the diagnosis process of FIG. 3 according to one example.

FIG. 3 is a flowchart of a diagnosis process using the ultrasound device 124 according to one example. FIG. 4 illustrates an application illustration of the diagnosis process of FIG. 3 according to one example. In the example illustrated in FIG. 4, the technician operating the ultrasound device 124 identifies the area of injury of a patient at step S300. This is illustrated as the area below the surface of the chest of a patient between an outer plural membrane and inner plural membrane.

The technician then applies a main beam approximately orthogonally to the area of injury via the first transducer probe 125a at step S302. In one example, frequencies for the main beam, such as 100 KHz, 1 MHz and 3 MHz, can be set for application to the injury such that they do not interfere with the second transducer probe 125b emitting a secondary beam at frequencies such as 6.5 MHz. In one example, the main beam applied by the first transducer probe 125a is pulsatile which can provide enhanced vibration profiles for detection by the second transducer probe 125b. The second beam applied by the second transducer probe 125b can also be pulsatile. It should be noted that the shape of the beam is not limited to that illustrated in FIG. 4 and both beams could alternatively be either radial or rectangular.

The second transducer probe 125b is then used to apply a secondary beam to the area of the injury to receive signal data 118 for generating image data 116. In one example, the first transducer probe beam is applied around the area of the injury while the second transducer probe beam is positioned directly at the area of the injury. However, other combinations could be applied as to where one or more of the beams are applied with respect to the injury. In one example, the first transducer probe 125a beam used to create a stirring effect within the tissue is applied at a predetermined angle of separation, such as 20-30 degrees, from the second transducer probe 125b. A specific angle of separation can be determined based on a depth (D) and a lateral separation distance (T) of the two transducers, wherein the angle of separation is the arc-tangent of T/D when one of the transducers is approximately perpendicular to the skin above the region of consideration. Therefore, the angle of separation is determined such that a beam of the first transducer probe 125a and a beam of the second transducer probe 125b intersect at an area of the injury. The depth can be determined as an average depth for the given patient body type which can be obtained from the anatomy data 114. Additionally, a user of the system 102 can estimate the thickness of fat over the area of injury, possibly by palpitating as would be understood by one of ordinary skill in the art, and add this thickness to the depth determination. Alternatively, or in addition to, the averaged depth and/or thickness of fat can be determined from the delay of the signal returned to the second transducer based on anatomical consideration of the tissue below the skin surface that is being diagnosed.

The separation (T) prevents interference in the signal reception by the second transducer probe 125b during imaging of the area at step S304 thereby allowing more accurate signal data 118 to be obtained for use in generating image data 116. For example, the separation allows the stirring beam of the first transducer probe 125a to cause a very small approximately perpendicular oscillation of the interface while at the same time causing a parallel or sliding motion, or "shear." This sliding or shearing motion is at a different phase than a perpendicular motion due to a known difference in bulk versus shear acoustic properties. Accordingly, there is a net elliptical motion generated which causes small eddies within a millimeter of a tissue interface where there is considerable difference in acoustic impedance across the interface. These minute eddies can be detected during image processing as indicating hemorrhages, exudates, edema and other injuries within the patient as further described herein.

In an example where neither of the first transducer probe 125a and second transducer probe 125b are applied orthogonally to the area of the injury, two angles of separation can be calculated based on a depth (D) determined similarly as described with respect to FIG. 3, and a lateral separation distance (T) of each respective transducer probe, wherein the first transducer probe 125a is applied at a distance (T1) from a vertical bisector of an approximate line through the middle of tips of the probes on the skin at the area of the injury and the second transducer probe 125b is applied at a distance (T2) from the vertical bisector, wherein a first angle of separation for the first transducer probe 125a is the arc-tangent of T1/D and a second angle of separation for the second transducer probe 125b is the arc-tangent of T2/D.

In all examples regarding placement of the first transducer probe 125a and the second transducer probe 125b, the CPU of the ultrasound device 124 can communicate with the first transducer probe 125a and the second probe 125b via the Bluetooth®, which is a registered certification mark of Bluetooth Sig, Inc., communication protocol or other communication protocol to ensure a proper angle of separation (T) or angles of separation (T1, T2) between the devices. This can be determined based on the use of accelerometers in the transducer probes at which point visual, tactile and/or sound can be used by the ultrasound device 124 to alert the user as to when the proper distance or placement with respect to the first transducer probe 125a and second transducer probe 125b is achieved.

Alternatively, in one embodiment and as illustrated in FIG. 4, the ultrasound device 124 can have a single transducer probe that produces both high-frequency sound waves aimed at exciting vibration in fluid pools while also receiving signal data 118 using Doppler. This embodiment provides for a more compact device to be employed and reduces manufacturing costs. The embodiment provides functionality even when these two beams are almost parallel but the Doppler color patterns can be somewhat different than when the beams are at a significant angle at their intersection such as 10 to 20 degrees.

Once the area has been imaged at step S304, the image data 116 is generated by the ultrasound device 124 and/or image generation engine 106 from the signal data 118 as described herein and is stored in the database 112. The image data 116 includes a linked time-series of images based on readings generated by the ultrasound probe 125b showing the movement and/or size of fluid at the area of the injury. Once the image data 116 is generated at step S304, the image processing engine 108 proceeds to process the image data 116 at step S306. As described herein, the noise level generated by the ultrasound device 124/132 and/or the patient themselves is identified at step S204 and further in FIG. 12 and is used during the image processing step S306.

To remove the noise at step S306, a variety of de-noising methods can be applied as further described in *Noise Reduction in Medical Ultrasound Image*; Benes, Radek and Riha, Kamil (Electorevue, Vol. 2, No. 3, September 2011), the entirety of which is herein incorporated by reference. Further, filters can be used to reduce the noise levels generated by the movement of the patient. For example, excessive Doppler detections greater than a predetermined noise threshold can represent movement by the patient rather than the detection of a specific pooling of liquid and can therefore be removed by the CPU of the ultrasound device 124 and/or image generation engine 106. Once the noise has been removed at step S306, the image data 116 can be more accurately analyzed by the image processing of step S306.

The image processing engine 108 can process the image data 116 to generate analysis data 120 which can be included in report data 122. The image processing of step S306 includes identifying and comparing areas of red/blue detected by color Doppler, or the shades of yellow typical of power Doppler, which indicate the movement of fluid to a predetermined size threshold. The identifying of the areas for comparison can be achieved by pattern recognition as further described herein with respect to at least FIGS. 12 and 13. The comparing can be performed by the CPU over a portion or the entire time series of segmented image data 116 by comparing the size of each detected area to a predetermined size threshold and generating an average over the entire time sequence as further described with respect to at least FIGS. 12 and 13. If the average size of detected fluid area is greater than the predetermined size threshold, the image processing engine informs the notification engine 110 to generate analysis data 120 indicating that abnormal fluid or air is detected at step S308. Alternatively, the notification engine 110 can generate an indication of abnormal fluid or air when a single time segmented piece of image data 116 includes a size of a colored fluid pool that is greater that a predetermined single-size threshold that can be the same or different from the predetermined size threshold.

In one exemplary application, the first transducer probe 125a can apply a beam incremented in frequency over time from a low frequency (i.e., 40 Hz) to a higher frequency (i.e., 1 MHz), seeking one or more peak values of motion as determined from the analysis data 120 of the image data 116. Once the peak values have been determined, the frequency of the beam of the first transducer probe 125a which correspond to these peaks values can then be set as the frequency for use in diagnosis of the injury.

The image processing engine 108 can detect abnormalities, such as bleeding or air pockets, at step S308 when a movement velocity of fluid in the diagnosed area is greater than a predetermined velocity threshold over a predetermined amount of time-linked image data 116. The movement velocity can be calculated based on the movement of fluids over a predetermined series of time-linked image data 116. Additionally, one or both of the size threshold and single-size threshold methods can be combined with the velocity threshold method to provide a combination of methods for determining the detection of injury, such as bleeding. For example, each method can output a score indicating the likelihood of injury based on the severity of numeric difference with the various thresholds and the scores can be added or averaged and compared to a score threshold to determine a likelihood of injury. Optionally, the image processing engine 108 can use the anatomy data 114 of the patient to identify particular thresholds for each detection methodology that are particular to the patient or a class of the patient. The various thresholds can, in one example be, taken as the noise level of red or blue appearances when there is no pool which can be determined based on a reading of signals by the second transducer probe 124b caused by the transducer probe 124a main beam over a region of the body which is known to not have a pool of fluid or air. This can be done at the time of the examination or based on the anatomy data 114 of the patient from previous readings or a general number from prior empirical readings of a variety of patients. In an exemplary embodiment, bleeding in particular can also be detected from the image data 116 as further described in U.S. Publication No. 2016/0239959, the entirety of which is herein incorporated by reference.

The analysis data 120 generated at step S306 is then included in report data 122 at step S312 and provided to the user via a display screen of at least one of the ultrasound devices 124/132, injury diagnosis system 102 and remote device 126/130. The report data 122 can include a diagnostic accuracy indication based on the score data generated by the image processing engine 108. For example, a color coding scheme could be provided that indicates the likelihood of abnormalities (i.e. green=likelihood of abnormality, yellow=moderate risk of abnormality and red=unlikely risk of abnormality or no decision could be made). The likelihood of an abnormality can be tied to the score computed by the image processing engine 108. Additionally, or in the alternative, audible alerts can be emitted based on the likelihood of an abnormality as detected by the image processing engine 108 and included in the report data 122. For combat situations where visual aids or sound aids may be dangerous or not practical, varied tactile feedback can be provided by the injury diagnosis system 102 to alert the technician of the severity and/or type of the injury.

The report data 122 can also include critical life-saving information such as the particular diagnosis and an indication of whether the patient should be moved immediately or should remain at the site of the injury. Further, the report data 122 can include suggestions for action by the technician based on the diagnosis such as surgery or stabilizing of the patient. These suggestions can also be influenced by the anatomy data 114 of the patient thereby providing diagnosis options that are particular to the patient.

If an abnormality is not detected at step S308, the image processing engine 108 informs the notification engine 110 that no abnormalities have been detected. The notification engine then inquires whether the user wishes to test a new spot or repeat the diagnosis at step S310. If the user desires a new test then the process proceeds to reidentifying the area of injury at step S300. Otherwise the process ends with respect to this particular diagnosis of the patient.

Accordingly, the injury diagnosis system 102 and diagnosis method images an induced scintillation in standard color Doppler or power Doppler imagery due to small movements near the surfaces/borders of organs and within a given fluid pool up to a distance into the pool over several wavelengths of the exciting sound. Accordingly, miniscule fluid pools indicating hemorrhages can be accurately detected by the system 102 which are not influenced by the volume or shape of the pool. Accordingly, the system 102 provides various improvements and practical applications to the technical field of ultrasound detection as well as diagnosis of injuries, such as hemorrhages, and provides a technical solution to the technical problem of accurately identifying internal injuries in patients based on signal analysis.

Figure 5A:
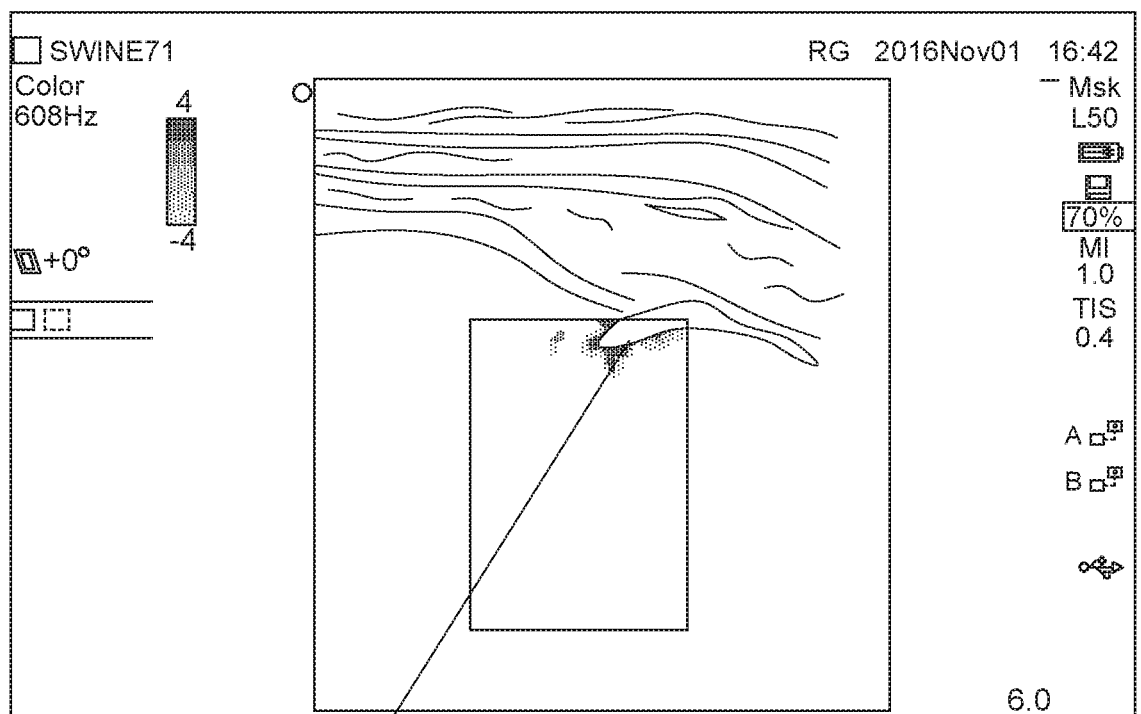
FIGS. 5A and 5B illustrate outputs of the system based on the diagnosis process of FIG. 3 according to one example.
Figure 5B:
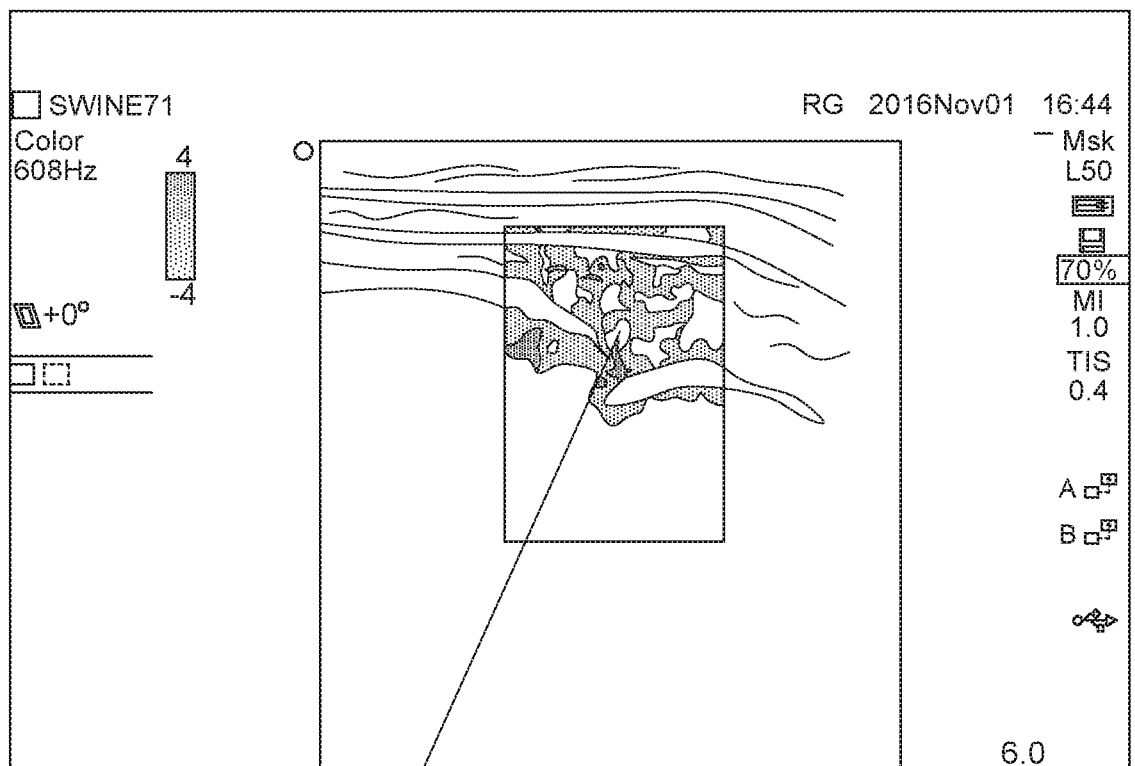

FIGS. 5A and 5B illustrate outputs of the injury diagnosis system 102 based on the diagnosis process of FIG. 3 according to one example. As illustrated in FIG. 5A at A, there is an unusual occurrence in ultrasonography where a flap of membrane above a hemothorax breaks away from the rest of the membrane thereby indicating a source of an abnormality. In color Doppler mode inside the box, the flap is outlined by a scintillating pattern which will make the pattern recognition system described herein more accurate in segmenting tissue structures and diagnosing injuries. With respect to FIG. 5B, this figure illustrates more of the upper membrane structure of FIG. 5A as the box is moved upwards. Here, the scintillations occur near membranes indicating increased reflections from the interfaces between membranes and fluids, that is, the impedance mismatch of the transition. Accordingly, this is where the image processing engine 108 of the injury diagnosis system 102 has identified areas of potential abnormalities, such as bleeding, based on an analysis of the image data 116. The operator and/or injury diagnosis system 102 can then perform further analysis to identify the likelihood of abnormalities at this location as well as any applicable treatment options.

Figure 6:
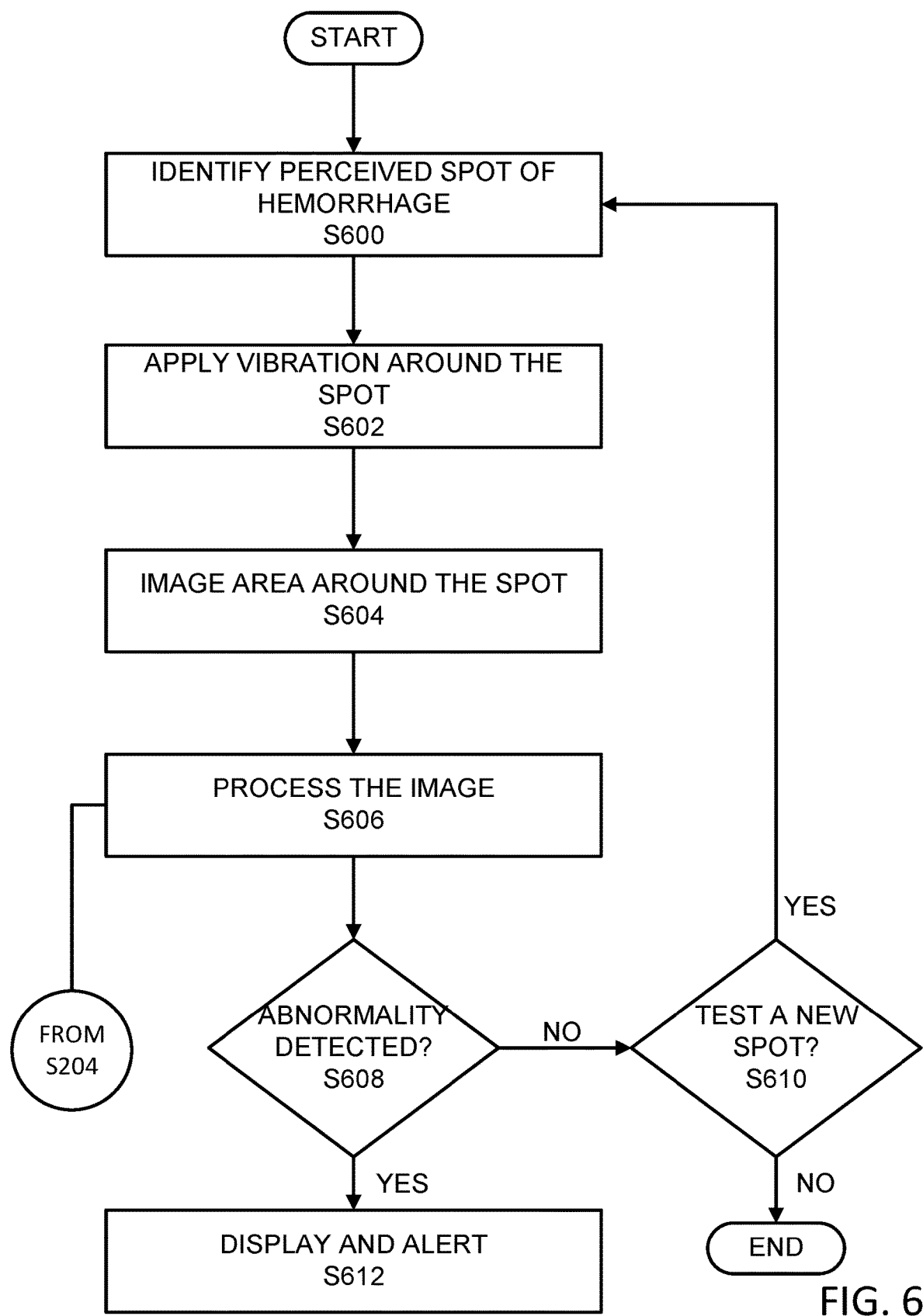
FIG. 6 is a flowchart of a diagnosis process according to one example.
Figure 7:
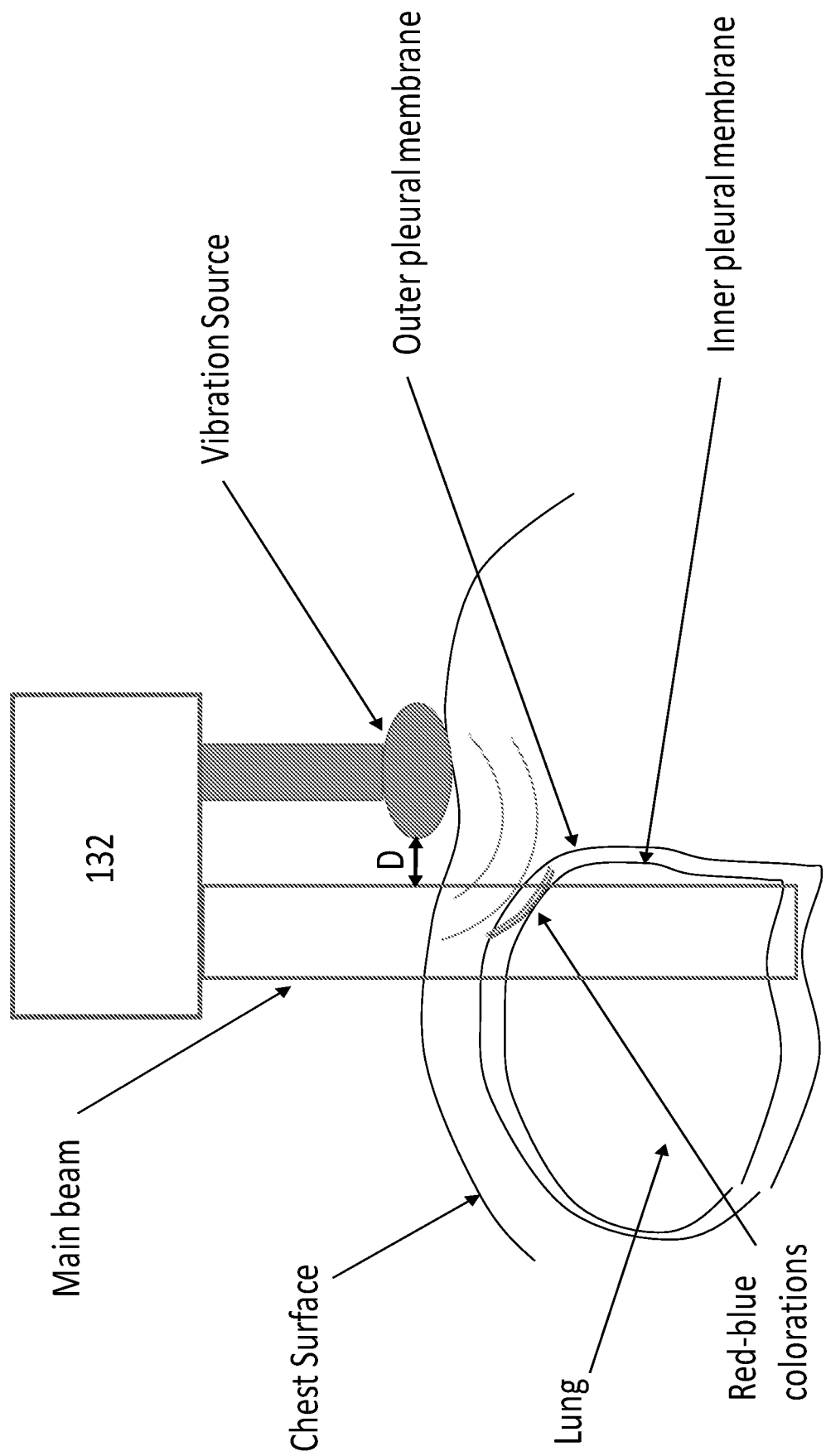
FIG. 7 is an application illustration of the diagnosis process of FIG. 6 according to one example.

FIG. 6 is a flowchart of a diagnosis process using the ultrasound device 132 according to one example. FIG. 7 illustrates an application illustration of the diagnosis process of FIG. 6 according to one example. In the example illustrated in FIG. 7, the technician operating the ultrasound device 132 identifies the area of injury of a patient at step 600. This is illustrated as the area below the surface of the chest of a patient between an outer plural membrane an inner plural membrane.

The technician then applies a vibration at or near the area of injury via the vibration device 133 at step S602. In one example, a specific range of frequencies for vibration device 133, such as 10 Hz to 1000 Hz, are applied to create the more telling Doppler patterns for use in the diagnosis of the injury. For example, the sensing of a spectrum in such a low-frequency range can show peaks in reflected energy at certain characteristic frequencies depending on a thickness of a blood pool and tissue interface in the direction of the applied force. Further, at certain frequencies the interference patterns at the transducer probe 131 can become less random and steadier. In a particular implementation and as further described with respect to at least FIGS. 12 and 13, vibration frequencies can be tested by stepping within a known range, such as 40 Hz to up to about 100 kHz, to provide enhanced results. Further, the vibration applied by the vibration device 133 can be pulsatile which can provide enhanced vibration profiles for detection by the transducer probe 131. Further, different frequencies can be applied by the technician or automatically by the CPU of the ultrasound device 132 via the vibration device 133 based on the size and/or shape of a detected pool of liquid. Thus, specific frequencies can provide better readings based on the size and/or shape of the pool. Accordingly, in one example, image data 116 can be compared to a stored database of pooled liquid images correlated to a table of frequencies to identify an optimal frequency for additional imaging which can then be automatically applied to the vibration device 133. Alternatively, or in addition, a pad having a plurality of vibration devices 133 could be fastened to a patient near the area of injury which can be used for continuous monitoring of injuries and to check for the growth of any hemorrhages.

The vibration device 133 causes fluids in pockets to slosh at certain to and fro modes of vibration with movement greater in the fluid than in the surrounding organs. The transducer probe 131 is then used to apply a beam to the area of the injury to receive signals for generating image data 116 based on Doppler frequency shifts in the fluid more than the tissue. In this example, the vibration device 133 is applied a distance D from the area of the injury while the transducer probe 131 beam is positioned approximately orthogonally to the area of the injury. The distance D is such that the movements of the skin generated by the vibration device 133 do not affect (i.e., wiggle) the readings of the transducer probe 131. In one implementation, the distance D is within the range of 20 cm to 40 cm from the application of the transducer probe 131 to provide for maximum vibration without affecting the readings of the transducer probe 131. With respect to this concern, the vibration device 133 can also be placed on a surface which does not directly couple with skin, fat and muscle under the probe.

Alternatively, or in addition to, the placement of the vibration device 133 and distance D can be based on the perceived location of the injury. For example, if the medical technician is concerned about an injury in an area that could relate to a Morrison's Pouch or Douglas Pouch or an injury near the spleen-lung, the vibration device 133 can be placed on the middle of the belly to provide for the best readings by the transducer probe 131. For sub-pubic areas, the vibration device 133 can be placed on the upper bellow or on the lower rib cage. The vibration device 133 is then used to create a stirring effect within the tissue by application near the injury which will be picked up by the transducer probe 131. In one example, the specific placement of the transducer probe 131 can be determined based on a known point on the skin for a particular pooling space. This area can be determined based on the FAST examination.

In all the discussed examples regarding placement of the vibration device 133 with respect to the transducer probe 131, the CPU of the ultrasound 132 can communicate with the vibration device 133 and transducer probe 131 via the Bluetooth® communication protocol or other communication protocol to ensure that a proper interference-preventing distance D between the devices before the vibration device 133 applies vibrations near the injury. Accordingly, visual, tactile and/or sound can be used by the ultrasound device 132 to alert the user as to when the proper distance or placement with respect to the transducer probe 131 and the vibration device 133 is achieved.

Sweeping or stepping vibration frequencies in a selected frequency range can then be applied by the vibration device 133 to the tissue surround the pool to produce a spectrum of color or power Doppler intensity versus frequency. This generates image data 116 having at least one peak in the spectrum corresponding to a fundamental mode of longitudinal vibration of the fluid as well as other peaks at harmonics or at peaks representing other modes in the motion of a fluid pool.

Once the area has been imaged at step S604 by the transducer probe 131, the image data 116 is generated by the ultrasound device 124 and/or image generation engine 106 from the signal data 118 as described herein and is stored in the database 112. The image data 118 includes a linked time-series of images based on readings generated by the ultrasound probe 131 showing the movement generated by the vibration device 133 and/or size of fluid at the area of the injury. Once the image data is generated at step S604, the image processing engine 108 proceeds to process the image data 116 at step S606. As described herein, the noise level generated by the ultrasound device 132 and/or the patient themselves is identified at step S204 and further in FIG. 12 and is used during the image processing step S306.

To remove the noise at step S606, a variety of de-noising methods can be applied as further described in *Noise Reduction in Medical Ultrasound Image*; Benes, Radek and Riha, Kamil (Electorevue, Vol. 2, No. 3, September 2011). Further, filters can be used to reduce the noise levels generated by the movement of the patient. For example, excessive Doppler detections greater than a predetermined noise threshold can represent movement by the patient rather that the detection of a specific pooling of liquid and can therefore be removed by the CPU of the ultrasound device and/or image generation engine 106. Once the noise has been removed at step S606, the image data 116 can be more accurately analyzed by the image processing of step S606.

The image processing engine 108 can process the image data 116 to generate analysis data 120 which can be included in report data 122. The image processing of step S606 includes identifying and comparing areas of red/blue detected by Doppler which indicate the movement of fluid to a predetermined size threshold. The identifying of the areas can be achieved by pattern recognition as further described herein with respect at least to FIGS. 12 and 13. Once the areas are identified, the patterns of color identified by Doppler indicate a multitude of information about the type of injury. Thus, the image processing engine 108 reviews the patterns based on at least one of color and location of the red/blue areas. The colors in the Doppler image data 116 indicate a location of an abnormality, such as a pool relative to nearby organs, where the relative position of the pool in turn indicates information about the type of hemorrhage. For example, a Morison's pouch between the liver and kidney often fills with blood after a blunt force or penetration to the abdomen. A pool of the blood forms on the right side of the abdomen yet the source of the blood is often from lacerations or holes in the spleen which is in the opposite side of the abdomen. The blood flows from the left side to the right side through channels between the organs. The image processing engine 108 can use image segmentation and corresponding pattern recognition to identify the hemorrhage and estimate the size of the pool by reviewing a sequence of patterns caused by the growth of the blood pool, pushing apart of the walls of the organs surrounding the blood pool and based on the shape of the pool. Thus, a spectral frequency analysis of the spectrum of color or power Doppler provides a very accurate verification of the presence of an abnormality such as a fluid pool.

Accordingly, the pattern recognition and spectrum analysis of the image processing engine 108 can more accurately generate analysis data 120 identifying the root cause of the injury and provide a more accurate diagnosis of the injury as well as treatment information particular to that injury in report data 122. The analysis data 120 generated at step S606 is then included in report data 122 at step S612 and provided to the user via a display screen of at least one of the ultrasound devices 132, injury diagnosis system 102 and remote device 126/130. The report data 122 can include a diagnostic accuracy indication based on the score data generated by the image processing engine 108. For example, a color coding scheme could be provided that indicates the likelihood of abnormality (i.e. green=likelihood of abnormality, yellow=moderate risk of abnormality and red=unlikely risk of abnormality or no decision could be made). Additional, or in the alternative, audible alerts can be emitted based on the likelihood of abnormality as detected by the image processing engine 108 and included in the report data 122. For combat situations where visual aids or sound aids may be dangerous or not practical, varied tactile feedback can be provided by the injury diagnosis system 102 to alert the technician of the severity and/or type of the injury.

The report data 122 can also include critical life-saving information such as the particular diagnosis and an indication of whether the patient should be moved immediately or should remain at the site of the injury. Further, the report data 122 can include suggestions for action by the technician based on the diagnosis such as surgery or stabilizing of the patient. These suggestions can also be influenced by the anatomy data 114 of the patient thereby providing diagnosis options that are particular to the patient.

If an abnormality is not detected at step S608, the image processing engine 108 informs the notification engine 110 that no abnormalities have been detected. The notification engine then inquires whether the user wishes to test a new spot or repeat the diagnosis at step S610. If the user desires a new test then the process proceeds to reidentifying the area of injury at step S600. Otherwise the process ends with respect to this particular diagnosis of the patient.

Accordingly, the injury diagnosis system 102 and diagnosis method images an induced sloshing movement in standard color Doppler or power Doppler imagery due to small movements near the surfaces/borders of organs and within a given fluid pool up to a distance into the pool over several wavelengths of the exciting sound. Accordingly, miniscule fluid pools indicating hemorrhages can be accurately detected by the system 102 based on a spectral frequency analysis of the spectrum of color or power Doppler. Accordingly, the system 102 provides various improvements and practical applications to the technical field of ultrasound detection as well as diagnosis of injuries, such as hemorrhages, and provides a technical solution to the technical problem of quickly and accurately identifying internal injuries in patients based on transducer signal data.

Figure 8A:
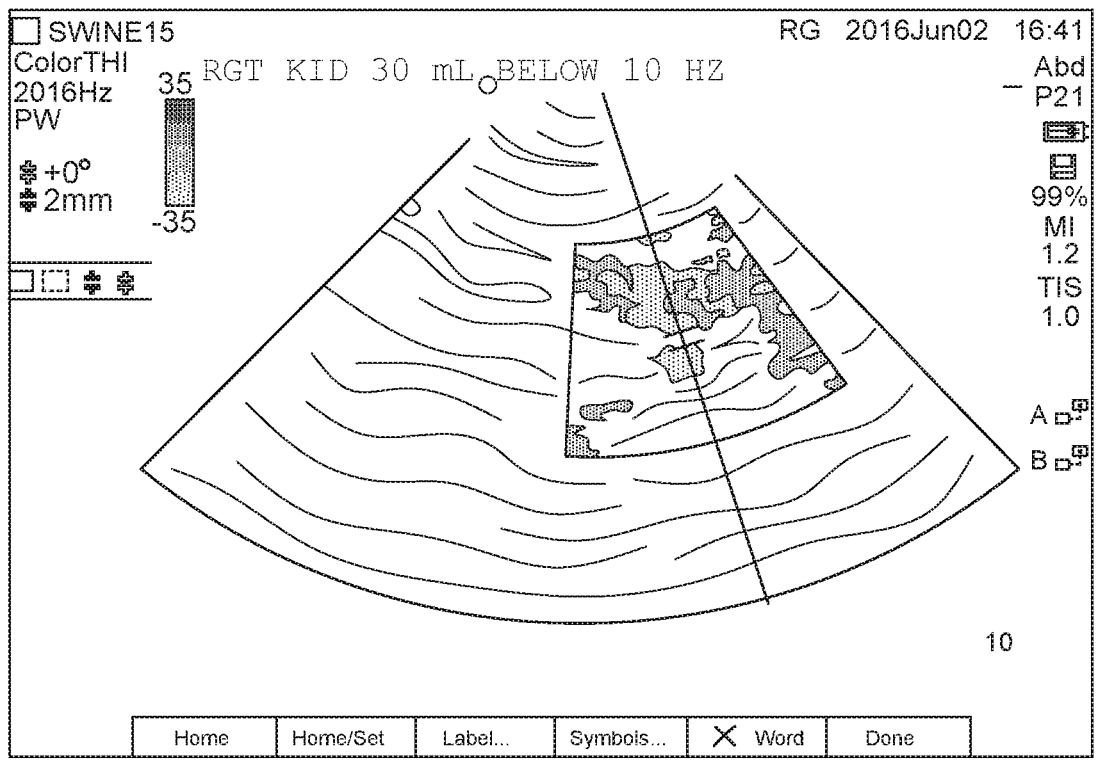
FIGS. 8-8F illustrate outputs of the system based on the diagnosis process of FIG. 6 according to one example.
Figure 8B:
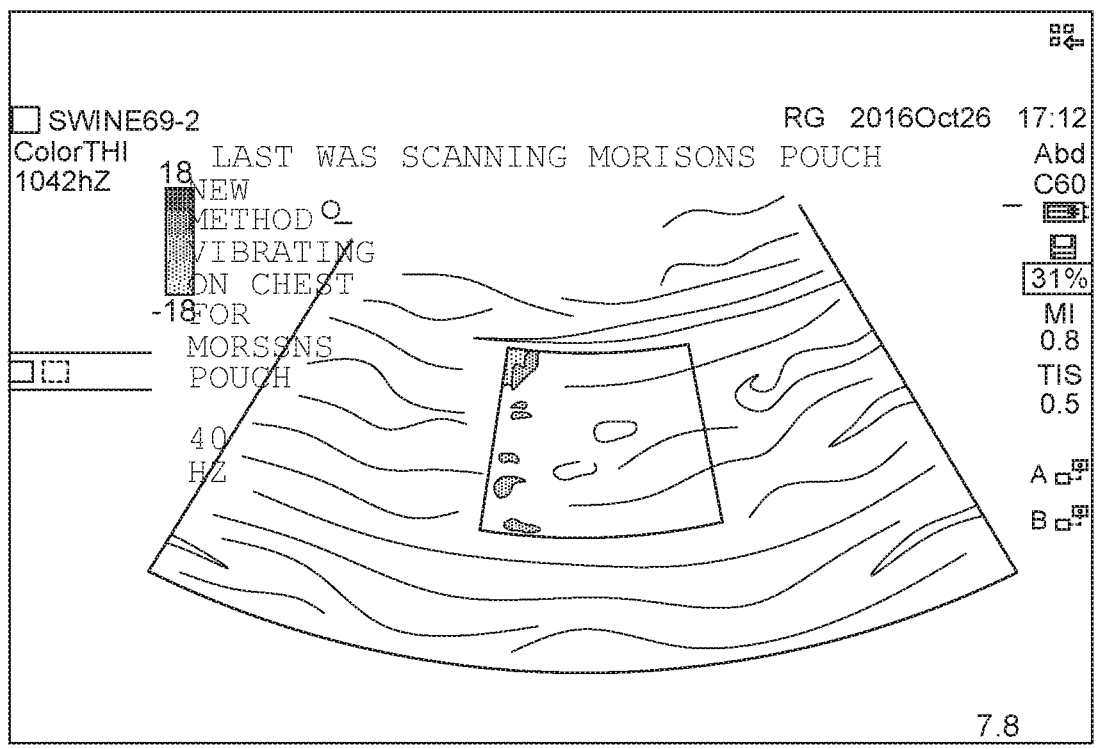
Figure 8C:
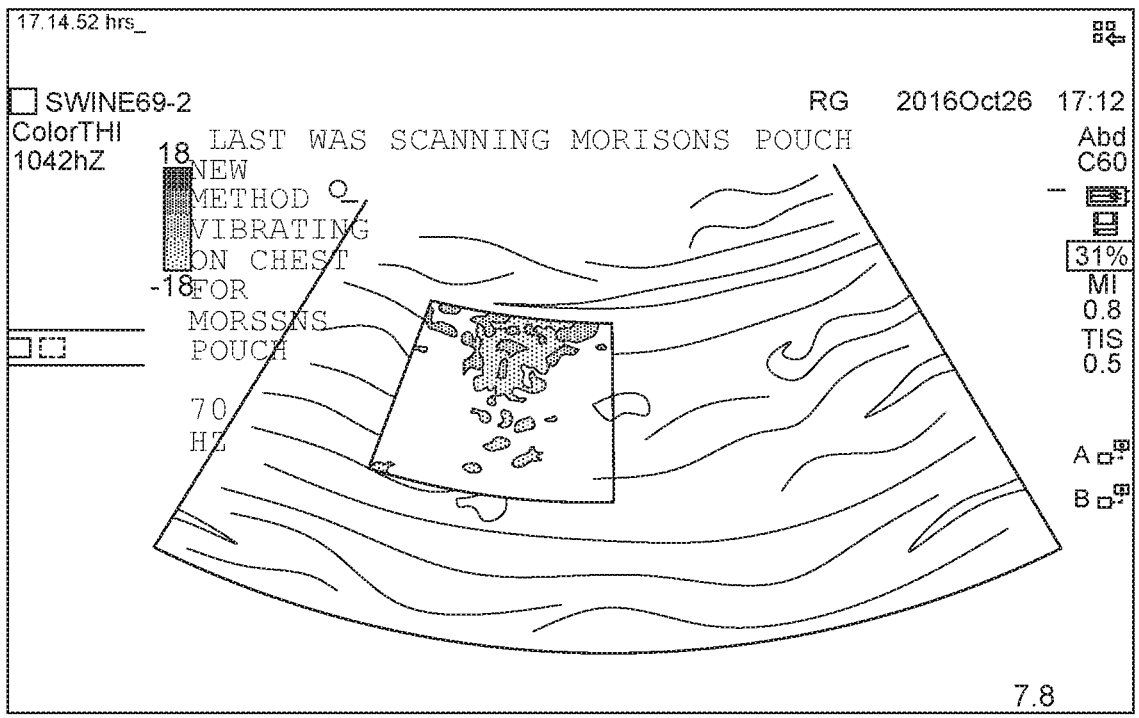
Figure 8D:
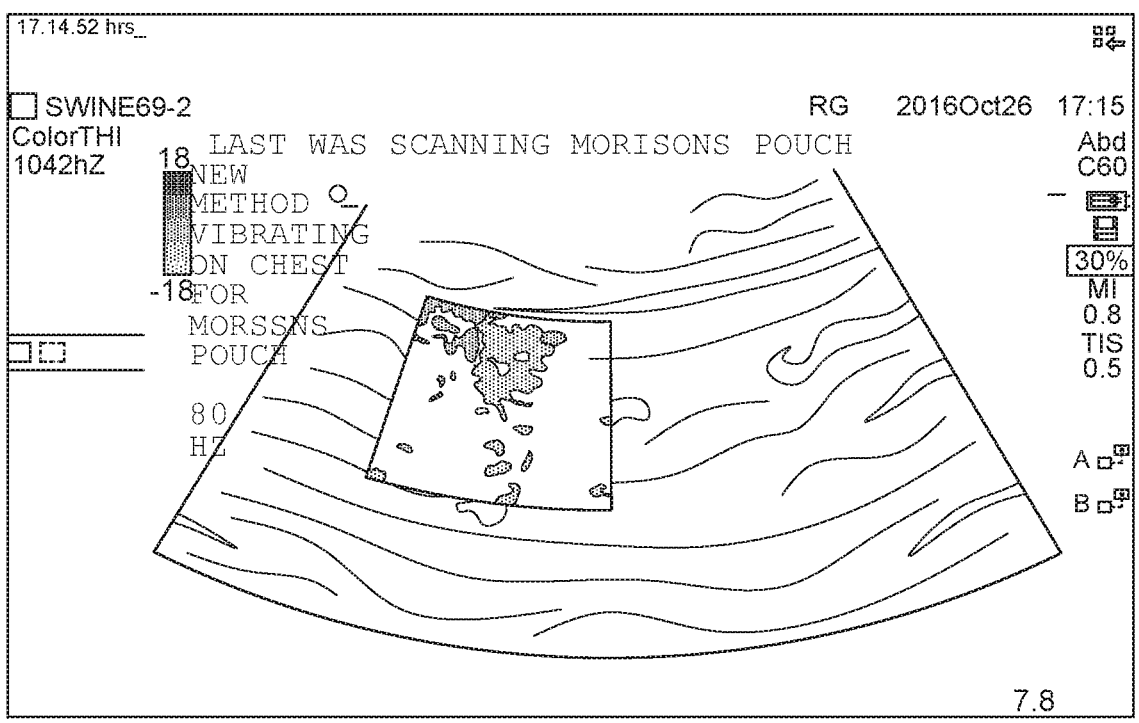

FIGS. 8A-8F illustrate outputs of the injury diagnosis system 102 based on the diagnosis process of FIG. 6 according to one example. As illustrated in FIG. 8A in the box, a pattern is obtained by the Doppler around the right kidney of a patient at 10 Hz with a 30 mL pool to the right of the kidney. FIGS. 8B-8D illustrate the application of 40 Hz, 70 Hz and 80 Hz, respectively, with the vibration device 133 at the chest wherein all depict 50 mL pools in a Morison's Pouch to the left of the kidney. The pouch is somewhat wedge-shaped with curved borders.

Figure 8E:
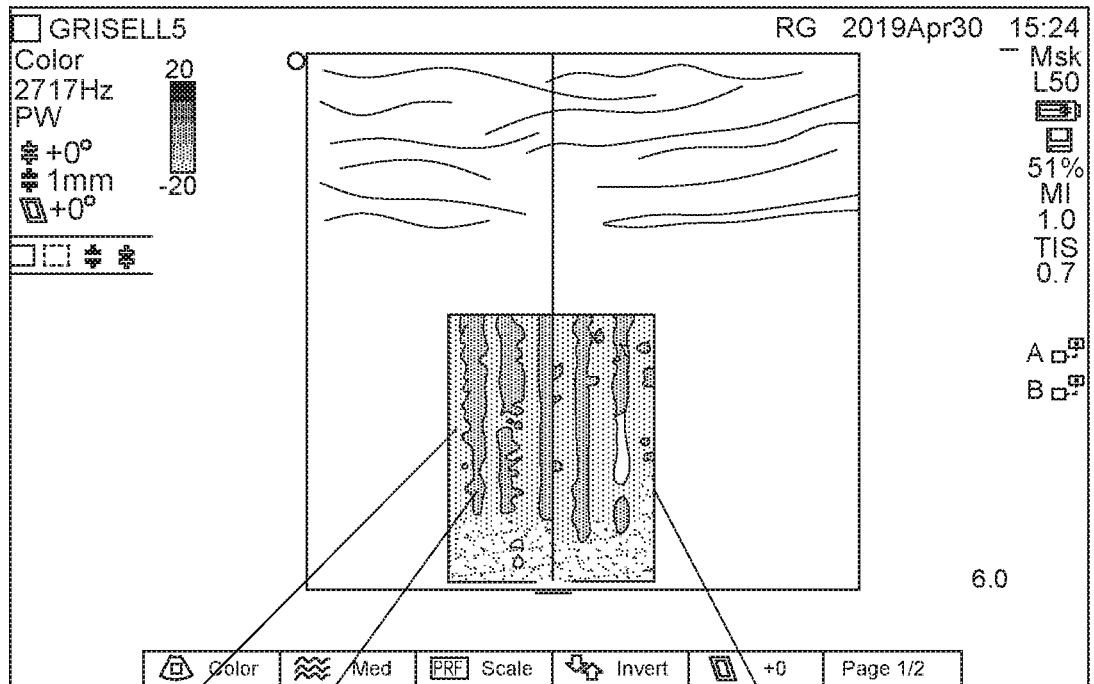

FIG. 8E illustrates a low-frequency vibration of 80 Hz which appears to best illuminate the fluid up to the internal side of a bladder, holding in this example about 200 milliliters. Importantly, while the depth and gain are not optimized for the lower membrane of the bladder, nevertheless it is highlighted along the bottoms of the red and blue columns. Hence, lower ends of red and blue columns touch the rather fuzzy inner bladder wall. Although not the case here, it is often fuzzy even when depth and gain are optimized because the bladder of a prone patient as in this example is accumulating sediments. This can be of advantage when the user is inexperienced, or in this example, it is impossible to go any deeper. FIG. 8E illustrates a rather full bladder, possibly 300 milliliters. The upper bladder wall is more distinct and appears so as to be at the upper ends of the colored columns. However, examiners are often most interested in the lower bladder wall, and whether there may be blood just beneath it. Accordingly, an array probe can be used instead of the linear probe to get deeper imagery.

Figure 8F:
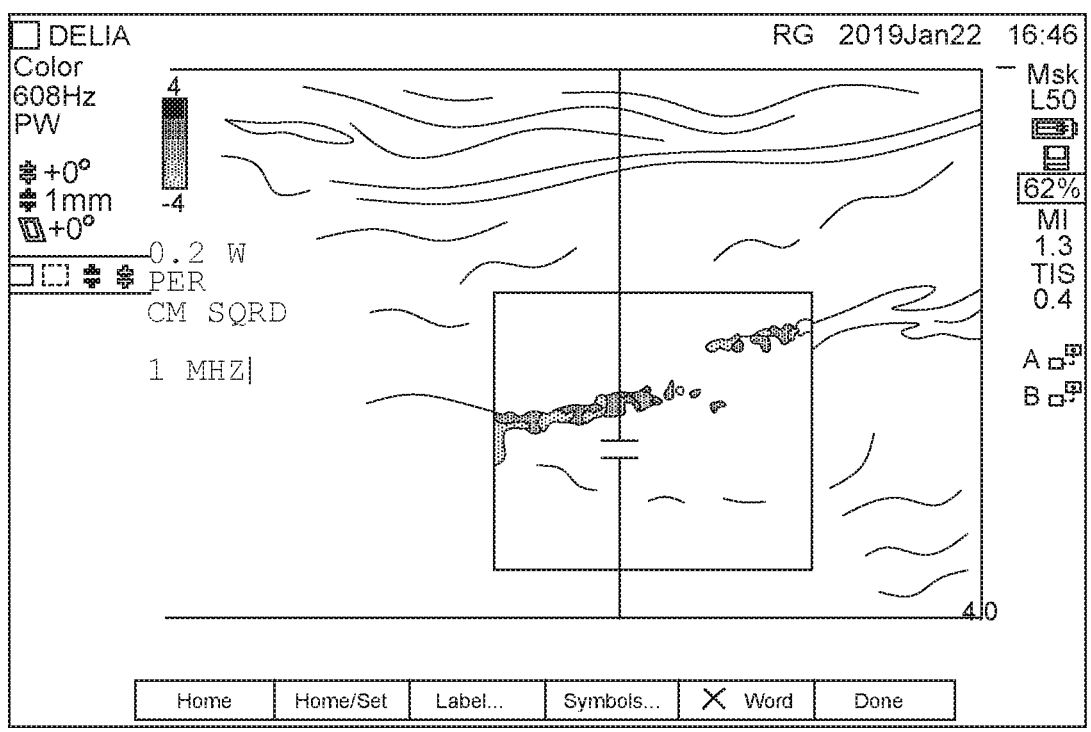

FIG. 8F illustrates a badly vasoconstricted femoral artery imaged at diastolic pressure (low between pulses) so it can be difficult to find in ultrasonic imagery without color enhancement. In this example, the vibration device is operating at a low power of 0.2 Watts per square centimeter and at 1 MHz in frequency. Thus, FIG. 8F illustrates how higher frequency vibrations such as at 1 MHz can highlight even a thin tissue interface containing lubricating fluid between membrane sheaths of the vastus medialus and sartorus muscles. This is useful in practice because the femoral artery can be hard to locate otherwise in seriously injured persons.

Accordingly, FIGS. 8A-8F illustrate where the image processing engine 108 of the injury diagnosis system 102 has identified areas of potential abnormalities based on an analysis of the image data 116. The operator and/or injury diagnosis system 102 can then perform further analysis to identify the likelihood of abnormalities at this location as well as any applicable treatment options.

For the process described in FIGS. 3 and 6, there are a variety of problems that can be introduced based on the particulars of a patient. For example, the height and girth of the patient near the organs of concern and the age of the patient can affect the location and spacing of organs. Further, fatty tumors can distort images shapes as well as the thickness of fat layers of a patient. Additionally, the thickness of fat and muscle over sub-pubic areas can require that the image processing engine 108 adjust the scan based on the depth at which it searches for spaces above and below particular areas. Further, the notification engine 110 can provide information to the medical technician with respect to the application of one or more transducer probes and/or the vibration device 133 based on pre-existing conditions of the patient. For example, the notification engine 110 could inform the operator that the patient has a hernia and that the operator may have to press the transducer probe 131/124a more deeply to minimize distortions due to the hernia. Additionally, a swollen prostate could cause the notification engine 110 to report that the operator must move or twist the transducer probes over a suprapubic area to assess the blood below it as well as superior to it. Accordingly, the ultrasound devices 124/132 can be calibrated such that the ultrasound devices 124/132 and the injury diagnosis system 102 can automatically adjust parameters based on the anatomy data 114 of the injured patient. Further, some of these problems can be minimized by the use of recently developed matrix arrays of small piezoelectric elements. These are phased arrays, which can scan larger regions than linear and curvilinear probes used in ultrasonography by scanning in two directions to produce 3D imagery. Thus, if there is a deviation from nominal physiology, the matrix array can detect the distorting around a fluid pool.

As noted herein, the injury diagnosis system 102 is connected to or includes processing circuitry of computer architecture. Moreover, processing circuitry configured to perform features described herein may be implemented in multiple circuit units (e.g., chips), or the features may be combined in circuitry on a single chipset, as shown in FIG.

Figure 9:
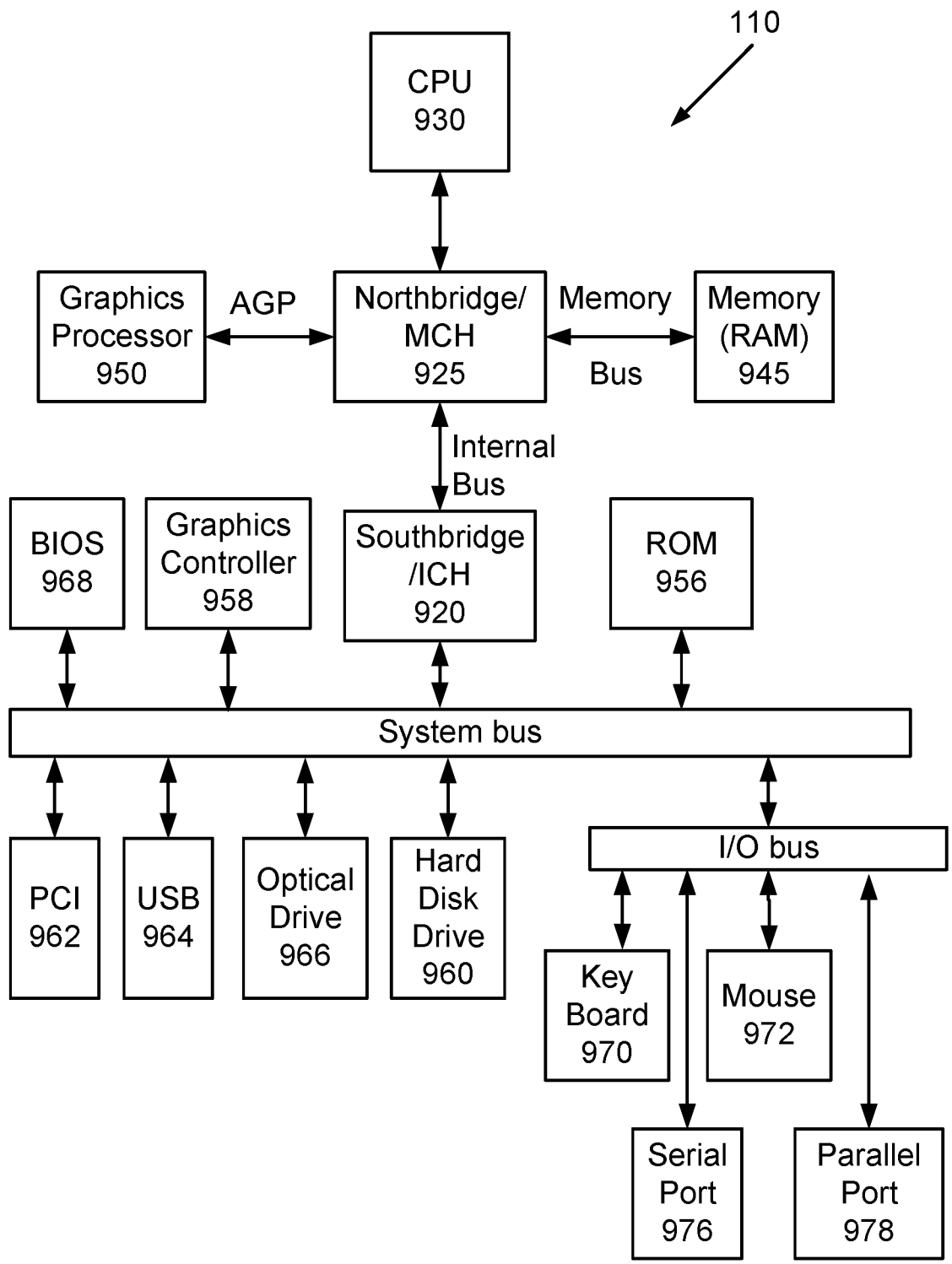
FIG. 9 illustrates various aspects of an exemplary architecture implementing a platform for diagnosing injures according to one example.

FIG. 9 shows a schematic diagram of a system 102 for diagnosing injuries, according to certain examples, for controlling the processing and providing the functionality described herein. The data processing system is an example of a computer in which code or instructions implementing the processes of the illustrative embodiments may be located.

In FIG. 9, data processing system 900 employs a hub architecture including a north bridge and memory controller hub (NB/MCH) 925 and a south bridge and input/output (I/O) controller hub (SB/ICH) 920. The CPU 930 is connected to NB/MCH 925. The NB/MCH 925 also connects to the memory 945 via a memory bus, and connects to the graphics processor 950 via an accelerated graphics port (AGP). The NB/MCH 925 also connects to the SB/ICH 920 via an internal bus (e.g., a unified media interface or a direct media interface). The CPU Processing unit 930 may contain one or more processors and even may be implemented using one or more heterogeneous processor systems.

Figure 10:
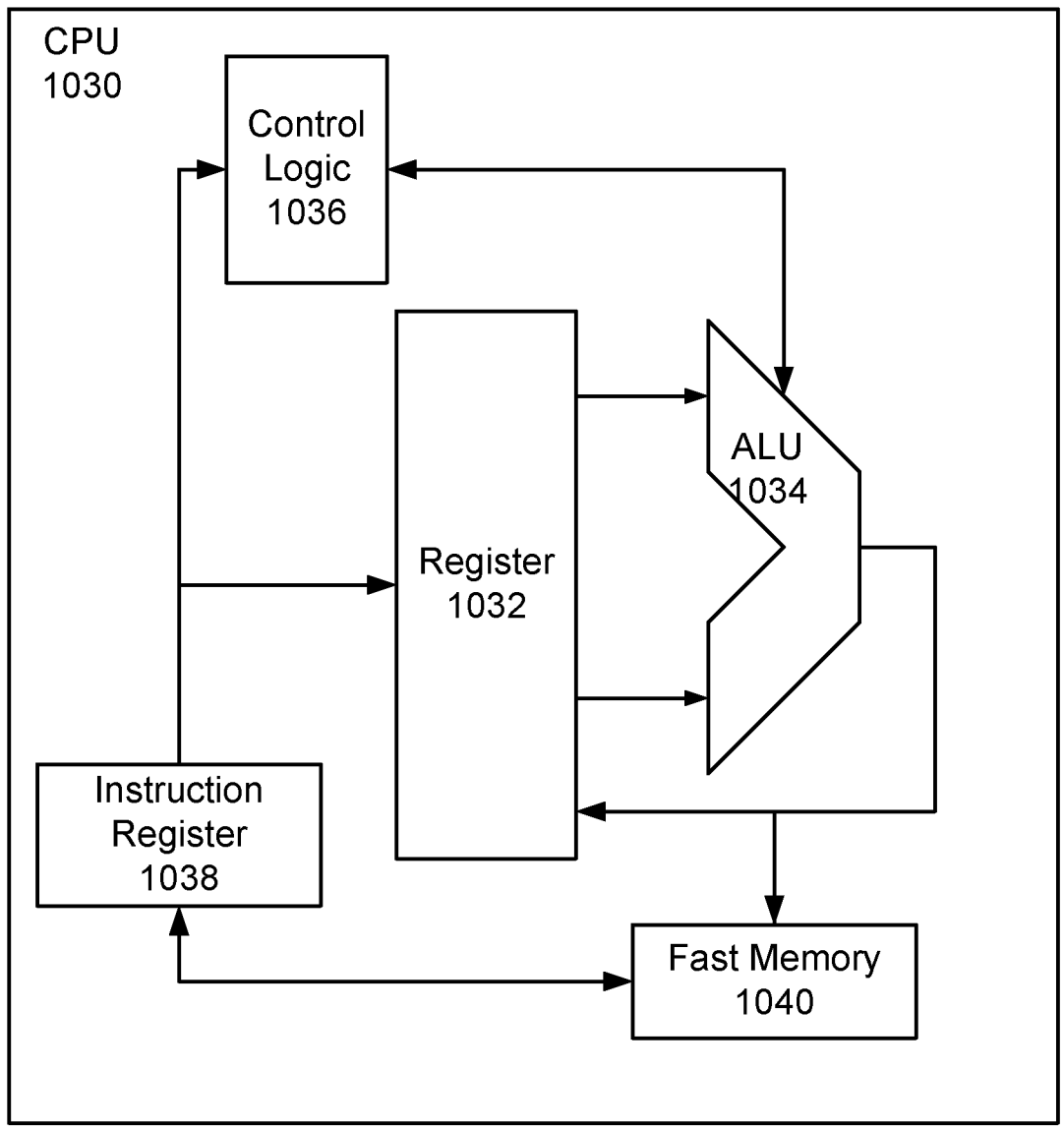
FIG. 10 illustrates the architecture of the Central Processing Unit (CPU) of FIG. 9 according to one example.

For example, FIG. 10 shows one implementation of CPU 1030. In one implementation, the instruction register 1038 retrieves instructions from the fast memory 1040. At least part of these instructions are fetched from the instruction register 1038 by the control logic 1036 and interpreted according to the instruction set architecture of the CPU 1030. Part of the instructions can also be directed to the register 1032. In one implementation, the instructions are decoded according to a hardwired method, and in another implementation, the instructions are decoded according a microprogram that translates instructions into sets of CPU configuration signals that are applied sequentially over multiple clock pulses. After fetching and decoding the instructions, the instructions are executed using the arithmetic logic unit (ALU) 1034 that loads values from the register 1032 and performs logical and mathematical operations on the loaded values according to the instructions. The results from these operations can be feedback into the register and/or stored in the fast memory 1040. According to certain implementations, the instruction set architecture of the CPU 1030 can use a reduced instruction set architecture, a complex instruction set architecture, a vector processor architecture, a very large instruction word architecture. Furthermore, the CPU 1030 can be based on the Von Neuman model or the Harvard model. The CPU 1030 can be a digital signal processor, an FPGA, an ASIC, a PLA, a PLD, or a CPLD. Further, the CPU 1030 can be an x86 processor by Intel® or by AMD™; an ARM® processor, a Power® architecture processor by, e.g., IBM®; a SPARC™ architecture processor by Sun® Microsystems or by Oracle®; or other known CPU architecture.

Referring again to FIG. 9, the data processing system 900 can include that the SB/ICH 920 is coupled through a system bus to an I/O Bus, a read only memory (ROM) 956, universal serial bus (USB) port 964, a flash binary input/output system (BIOS) 968, and a graphics controller 958. PCI/PCIe devices can also be coupled to SB/ICH YYY through a PCI bus 962.

The PCI devices may include, for example, Ethernet adapters, add-in cards, and PC cards for notebook computers. The hard disk drive 960 and the CD-ROM 966 can use, for example, an integrated drive electronics (IDE) or serial advanced technology attachment (SATA) interface. In one implementation, the I/O bus can include a super I/O (SIO) device.

Further, the hard disk drive (HDD) 960 and the optical drive 966 can also be coupled to the SB/ICH 920 through a system bus. In one implementation, a keyboard 970, a mouse 972, a parallel port 978, and a serial port 976 can be connected to the system bust through the I/O bus. Other peripherals and devices that can be connected to the SB/ICH 920 using a mass storage controller such as SATA or PATA, an Ethernet port, an ISA bus, a LPC bridge, SMBus, a DMA controller, and an Audio Codec.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 11, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

Figure 11:
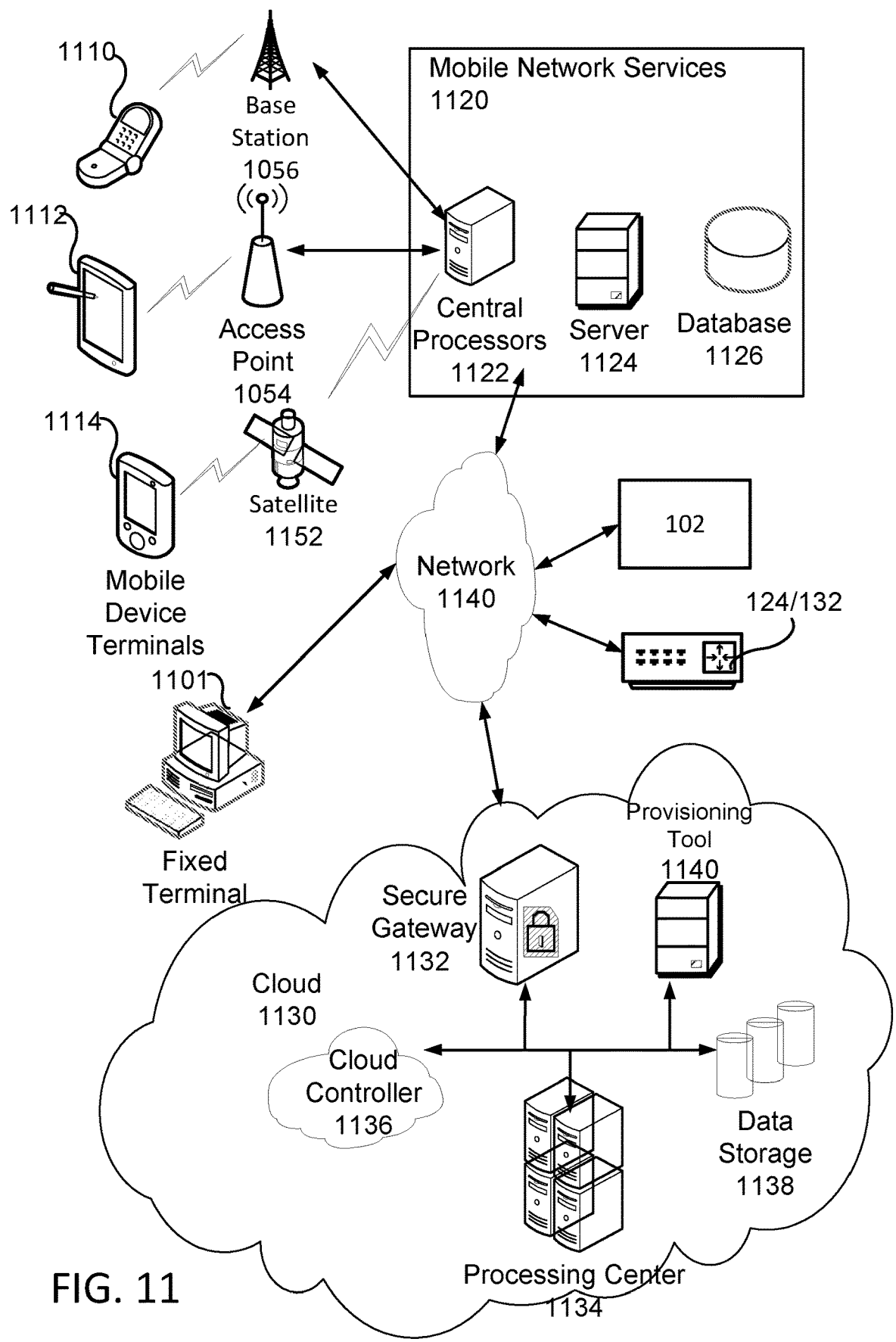
FIG. 11 illustrates a distributed system for connecting user computing devices with a platform for diagnosis injuries according to one example.

FIG. 11 shows an example of cloud computing, having various devices interconnected to each other via a network and cloud infrastructures. Similarly, FIG. 11 shows a PDS 1112 and a cellular phone 1114 connected to the mobile network service 1120 through a wireless access point 1154, such as a femto cell or Wi-Fi network. Further, FIG. 11 shows the injury diagnosis system 102 connected to the mobile network service 1120 through a wireless channel using a base station 1156, such as an Edge, 3G, 4G, or LTE® network, for example. Various other permutations of communications between the types of devices and the mobile network service 1120 are also possible, as would be understood to one of ordinary skill in the art. The various types of devices, such as the cellular phone 1114, a tablet computer 1116, or a desktop computer, can also access the network 1140 and the cloud 1130 through a fixed/wired connection, such as through a USB connection to a desktop or laptop computer or workstation that is connected to the network 1140 via a network controller, such as an Intel® Ethernet PRO™ network interface card from Intel® Corporation of America, for interfacing with a network.

Signals from the wireless interfaces (e.g., the base station 1156, the wireless access point 1154, and the satellite connection 1152) are transmitted to and from the mobile network service 1120, such as an EnodeB and radio network controller, UMTS, or HSDPA/HSUPA. Requests from mobile users and their corresponding information as well as information being sent to users is transmitted to central processors 1122 that are connected to servers 1124 providing mobile network services, for example. Further, mobile network operators can provide services to the various types of devices. For example, these services can include authentication, authorization, and accounting based on home agent and subscribers' data stored in databases 1126, for example. The subscribers' requests can be delivered to the cloud 1130 through a network 1140.

As can be appreciated, the network 1140 can be a public network, such as the Internet, or a private network such as an LAN or WAN network, or any combination thereof and can also include PSTN or ISDN sub-networks. The network 1140 can also be a wired network, such as an Ethernet network, or can be a wireless network such as a cellular network including EDGE, 3G and 4G wireless cellular systems. The wireless network can also be Wi-Fi, Bluetooth®, or any other wireless form of a communication that is known.

The various types of devices can each connect via the network 1140 to the cloud 1130, receive inputs from the cloud 1130 and transmit data to the cloud 1130. In the cloud 1130, a cloud controller 1136 processes a request to provide users with corresponding cloud services. These cloud services are provided using concepts of utility computing, virtualization, and service-oriented architecture. Data from the cloud 1130 can be accessed by the system 102 based on user interaction and pushed to user devices 1110, 1112, and 1114.

The cloud 1130 can be accessed via a user interface such as a secure gateway 1132. The secure gateway 1132 can, for example, provide security policy enforcement points placed between cloud service consumers and cloud service providers to interject enterprise security policies as the cloud-based resources are accessed. Further, the secure gateway 1132 can consolidate multiple types of security policy enforcement, including, for example, authentication, single sign-on, authorization, security token mapping, encryption, tokenization, logging, alerting, and API control. The cloud 1130 can provide, to users, computational resources using a system of virtualization, wherein processing and memory requirements can be dynamically allocated and dispersed among a combination of processors and memories such that the provisioning of computational resources is hidden from the users and making the provisioning appear seamless as though performed on a single machine. Thus, a virtual machine is created that dynamically allocates resources and is therefore more efficient at utilizing available resources. A system of virtualization using virtual machines creates an appearance of using a single seamless computer even though multiple computational resources and memories can be utilized according increases or decreases in demand. The virtual machines can be achieved using a provisioning tool 1140 that prepares and equips the cloud-based resources such as a processing center 1134 and data storage 1138 to provide services to the users of the cloud 1130. The processing center 1134 can be a computer cluster, a data center, a main frame computer, or a server farm. The processing center 1134 and data storage 1138 can also be collocated.

Figure 12:
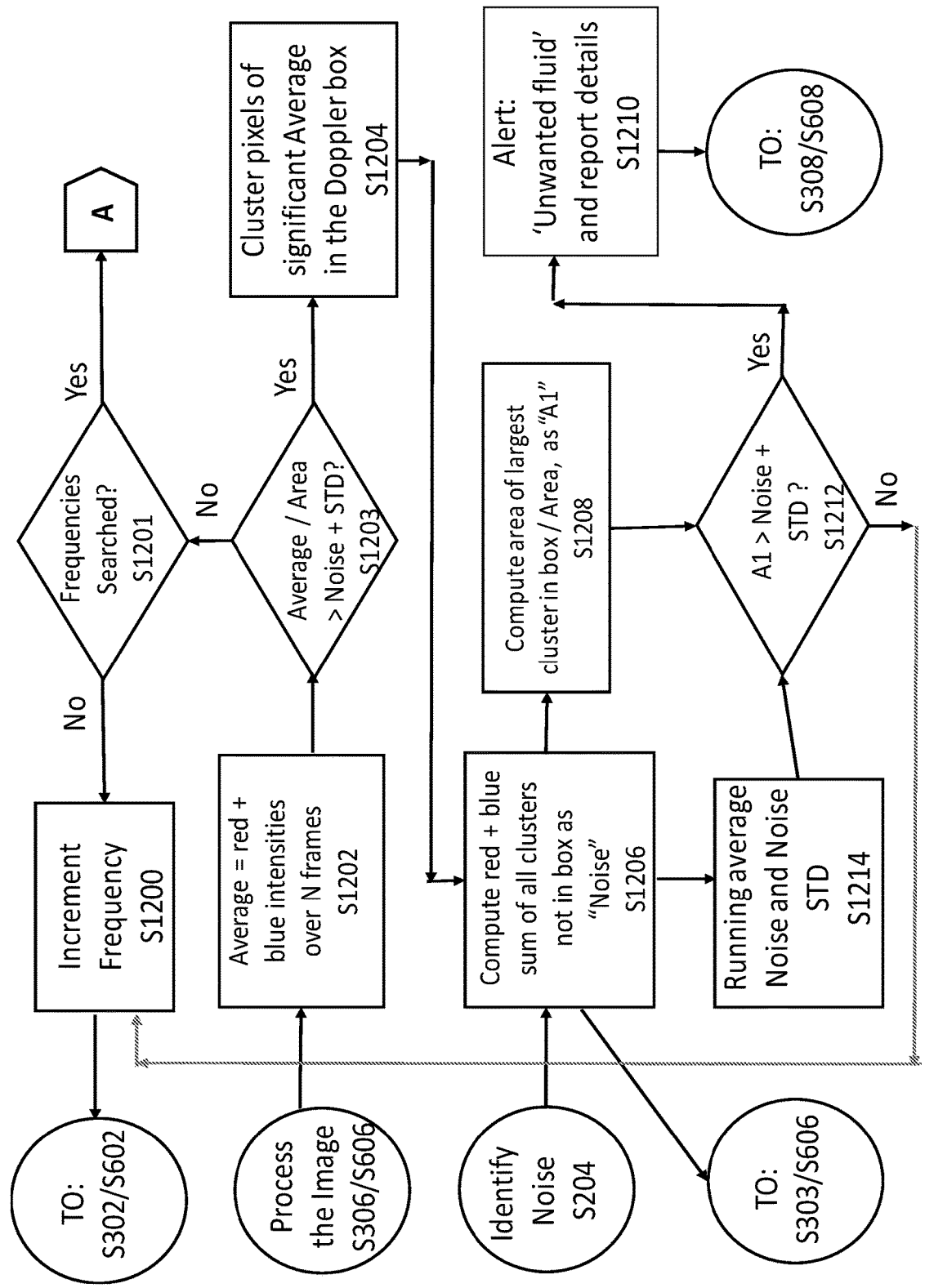
FIG. 12 illustrates a process for processing images according to one example.
Figure 13:
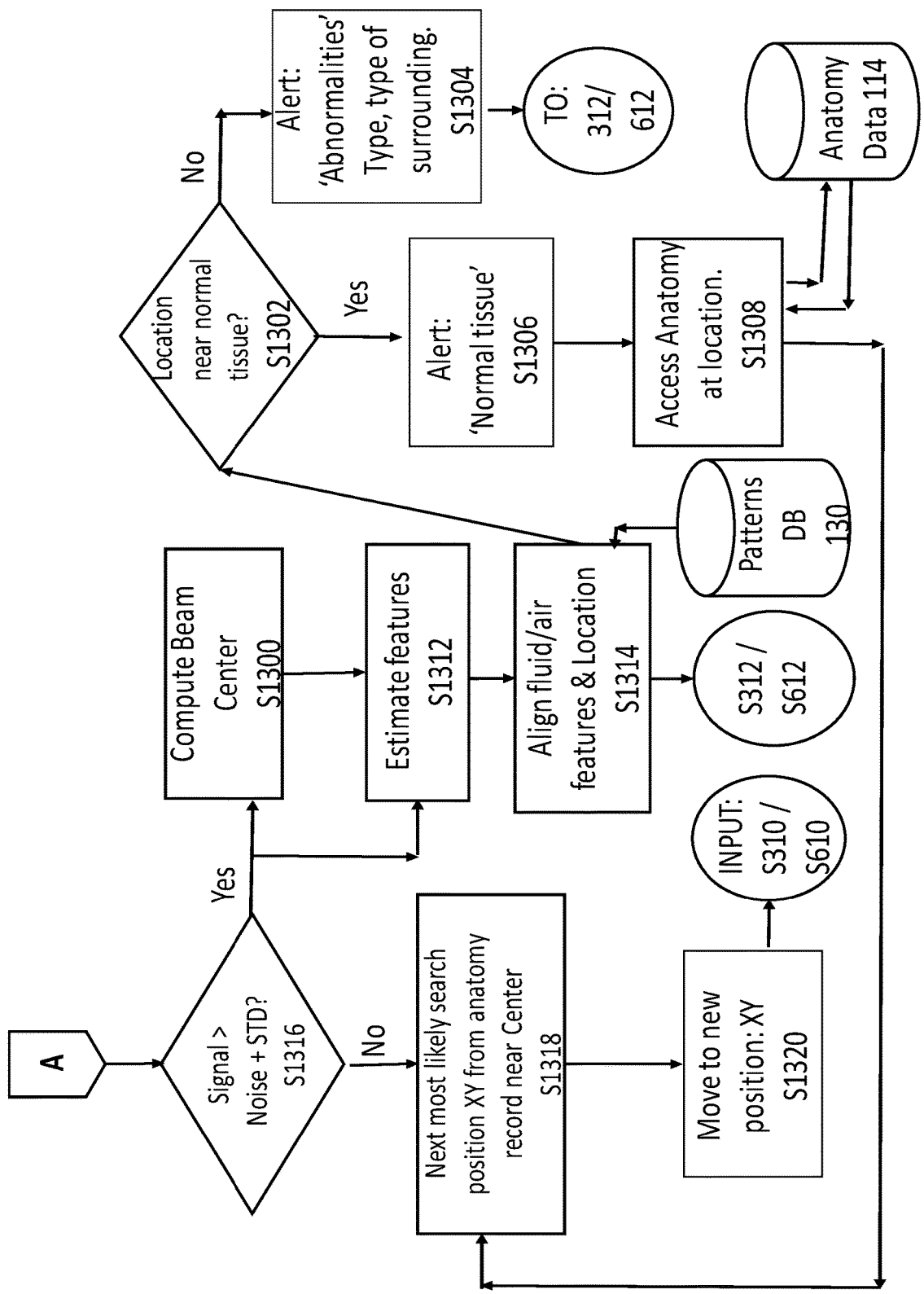
FIG. 13 illustrates further details of the process for processing images of FIG. 12 according to one example.

FIGS. 12 and 13 illustrate further details of the processing of images as initially described with respect to FIGS. 3 and 6. The steps preceding steps S306/S606 relate in part to exploring a number of frequencies of stimulation via high frequency ultrasound as in step S306 or low frequency vibrations as in step S606. Thus, in one example, the system may step or sweep through a single set of frequencies of stimulation which are most likely to vibrate the fluid or air in such a manner that when processed by the injury diagnosis system 102 provide a revealing, colorful pattern in imaging results, such as Doppler imaging. Another example can include a set range of frequencies to explore by incrementing a particular frequency as in step S1200. Thus, in one implementation, more detailed features of an abnormal or dangerous region are not computed until the frequency range has been searched, as in step S1201. The search may be cut short for either of two reasons: all stimulatory frequencies have been explored, in which case transition "A" leads to step S1316 of FIG. 13; or if a certain signal, the average of the sum of colors within the Doppler window calculated at step S1202 divided by the area of the Doppler window (i.e. the Doppler window of the given ultrasonic instrument determined by its particular settings and computational limitations to keep up with the given frame rate) is greater than a certain "Noise," (Noise+STD (standard deviation)). In this case, an alert will be displayed and a report generated at step S1210 via step S308/S608. As illustrated by step S1206, in one example, the noise can be a comparable sum of colors now outside the window, averaged by the area outside and averaged over N frames, just as is the signal inside the box. Thus, for example, a simple formula for noise can be an area-normalized sum of colors outside the Doppler box, as compared with a comparable sum of cluster colors inside it. Note that in one exemplary embodiment, the threshold in step s1212 could be adjusted to A1>Noise+M×STD if the system is reporting too many false positives with M>1. This threshold is a parameter that can be tuned to the particular user's preferences or automatically tuned based on a preference shared by a unit such as a hospital, clinic or ward.

Step S306 of FIG. 3 or step S606 of FIG. 6 provide inputs to an accumulating average over a certain specified number of frames, N, of the "total color intensity" (step S1202) which is the sum of red and blue intensities, that is, within the Doppler window (i.e. the rectangular or trapezoidal area which a given ultrasonic instrument will delineate based on its particular settings and computational restrictions). If average intensity normalized by the area of the instrument's Doppler window is greater than a fixed threshold such as the Noise+STD (step S1203), then in one example a further step would be to cluster pixels of non-zero total intensity at step S1204 by a well-known clustering algorithm such as Iso-Data, Memarsadeghi, N., Mount, D. M., Netanyahu, N. S., Le Moigne, J. (2007): A Fast Implementation of the ISO-DATA Clustering Algorithm. International Journal of Computational Geometry and Applications, 17, 71-103, the entirety of which is herein incorporated by reference. In this case, each cluster can then be assigned a "Border," for example, points which are within one or two wavelengths of the ultrasound in distance from closest pixels in the cluster. For the complex color shapes often obtained in such imagery, a clustering method is recommended because it avoids the computational complexity of edge or blob segmentation traditionally applied, since the color edges are jagged or otherwise difficult to close into a single closed curve. However, with any segmentation or clustering algorithm chosen, the next step herein is to compute the area of the largest cluster, denoted by "A1" (S1208).

If the corresponding average intensity inside the cluster boundary is greater than that of a comparable measure of the noise area outside the Doppler box, then an alert is displayed and report generated via step S1210 to the effect, "Unwanted fluid." Additionally, or alternatively, if the corresponding average intensity is greater than the Noise+some set fraction, M, of its standard deviation (STD) then an alert is displayed and report generated via step S1210 to the effect, "Unwanted fluid". If neither of these conditions is found, then the processing proceeds to increment the frequency at step S1200 to process additional images. With an automatic frequency sweeping or stepping capability, in the case that no total intensity is above zero after the range of frequencies is examined, then an alert is sent to the user that there is no unwanted, dangerous fluid as evidenced by color patterns in the current beam and an estimation of the next most likely position is made automatically as indicated in step S310/S610 and FIG. 13 at step S1306. This next most likely position is obtained from the anatomy database 114, where each small volume of a given body size and type in some reference coordinates is represented by a record containing likely tissue/fluid type, along with the "next most likely" area in which to look. This information is precomputed based on standardized body sizes such as GHBMC. The tissue types at various depths are not sensitive to a given patient's fat layer thickness (as estimated by the user) after correcting for (average—patient) fat thickness, since patients' fat layers are found predominantly under and perpendicular to the skin.

FIG. 13 illustrates more detailed functionality for identifying the location and type of bodily fluid (e.g. internal bleeding), as well as preferably the type of surrounding tissue encasing the same.

Once all the frequencies have been searched the process proceeds to FIG. 13S where it is determined at step S1316 if the area of total intensity is greater than a noise level computed at step S1214. In on example, the signal could be a maximum value of A1 normalized by area over frequencies searched. If so, then a "center" of the fluid is computed as a reference point at step S1300, e.g. the centroid of the colored area in the given beam for accurate alignment of the fluid/air inclusion with a pattern in the patterns database (DB) 130 (i.e., shape features of the fluid/air inclusion). This point, taking into account the offset from the center of the beam, is then compared with the center in the Image database. Another example of these signal or image processing steps contemplate image data being stored in a different manner appropriate to a classifier or neural network, having features of a classifier, or internal weights of a neural network, or similar process. Thus, other examples of processing include statistical classifiers, vector machines, and neural networks, each of which has somewhat different forms of "features" (S1312). For example, with typical training of a convolutional neural network, the "features" comprise a rather large set of "weights" applied in each "neuron" which typically applies a threshold to a non-linear function of its input, as suggested by the anthropomorphic term, neuron. For each location, generally there will be many actual color reverberation patterns from surfaces or volumes of different cavity shapes and sizes at given frequencies of ultrasound and vibration. At step S1314, these selected patterns are compared with the observed image or signal at the expected beam center by shifting up and down until a high correlation is obtained; otherwise the search continues (S1201). With comparisons of shape features of a fluid/air inclusion with a pattern in the pattern DB 130, such features as inclusion width, maximum thickness, and locations of corners (high curvatures in the border), are useful in alignment of the inclusion with the pattern.

As in step S1314, the observed data and a database entry are aligned, which can involve shifting the signal up or down relative to the pattern, or shifting the observed image up/down and left/right. However, the latter is computationally intensive so an example of so shifting an image is to move it several steps to the left and right, say M steps, and at each left/right shift, move up and down several more steps, say N; thus M×N image shifts are involved.

When it is determined at step S1302 that the location of fluid/air is near normal tissue, the prediction is ignored, a "normal tissue" alert is issued at step S1306, the anatomy location is accessed at step S1308, and the user is instructed to move to next-best location for imaging unwanted fluids if any at steps S1318 and S1320. In one example, "near" could be within a region of noise pixels or wholly inside the region of normal tissues according to the anatomy data 114. A good alignment with features within certain tolerances of those within a pattern is obtained as in S1302 where fluid/air features match with those of a pattern within certain tolerances, then the location is tested for being near regions of undamaged tissue, again making reference to the anatomy data 114 (arrows not shown). Tolerances could again be set as fractions of pattern feature values such as one-half or one-quarter, but again, standard deviations of feature values could be precomputed in the patterns DB 130, obtained for example by examining a large set of fluid/air images in human clinical data. To be "near" a region of normal tissue means either to overlap some noise pixels around the fluid/air contiguous with the referenced region, or to be wholly within the expected anatomical boundary of the normal tissue. Otherwise, if the fluid/air is abnormal (not expected for a healthy individual) then a "Alert" or report is made at step S1304 of the type of abnormality and type of surrounding tissue as may be visible on the screen. This information is contained in the Anatomy database 114.

The functionality described herein can differentiate "normal tissue" (S1306) from internal bleeding or other dangerous or unwanted bodily fluids or air (S1304) at a body region in the "beam Center" (S1300) and estimated depth. This depth can be the sum of average depth of the region obtained from the anatomy database 114. This database 114 could contain for example, G60man, G60woman, G100man, etc., and several other such standard body sizes and shapes defined by the GHBMC or other commonly employed three-dimensional body database delineating organ surfaces and fluid locations. If not included, such data should be augmented to include tissue/fluid/air type, surrounding fluid/ tissues types, as well as the "Next most likely search position" mentioned in step S1318.

Figure 14:
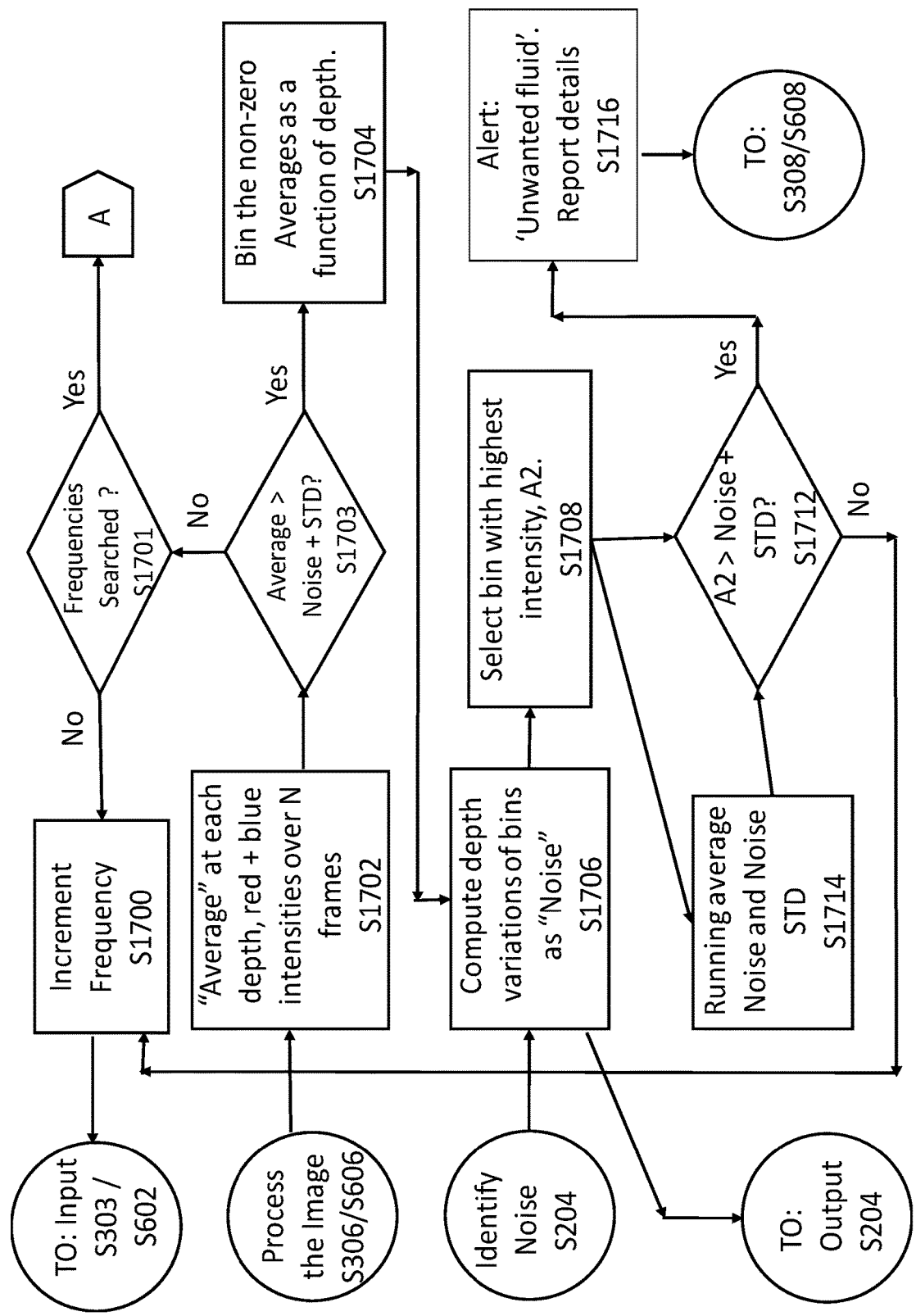
FIG. 14 illustrates a process for processing images according to one example.

FIG. 14 illustrates one example of processing according to steps S204 and S306/S606 which uses an "A-mode like" signal extracted from B-mode reflections as a function of depth. This signal constitutes a 1-dimensional array of sums of blue, or red, or total red plus blue intensity in horizontal slices of the image of one or more pixels in height, here termed "Bins." In other words, there is one bin at each depth of the instrument, or as another example, a series of slices at equally spaced depths of cross-sectional colorations across the width of the B-mode beam. Similarly, as in FIG. 12, the step S1700 and following input from either step S306 (high frequency method) or step S606 (vibrational), explore a number of frequencies of "stimulation" (high frequency ultrasound as in step S306 or low frequency vibrations as in step S606).

An example is to have a single, fixed frequency of stimulation which has been found in development or calibrations to most likely vibrate the fluid or air in such a manner that it shows a colorful pattern in Doppler imaging. Another example is to have a set range of say 100 frequencies to "explore" with the increment frequency step S1700. The search may be cut short for either of two reasons: all stimulatory frequencies have been explored, in which case off-chart "A" leads to 1316 as in FIG. 13 with the difference being that the patterns database 130 now contains color echograms or sonograms indicative of a variety of injury types (internal bleeding, exudates, edema, etc.). For each location, generally there will be many actual color reverberation patterns from surfaces or volumes of different cavity shapes and sizes at given frequencies of ultrasound and vibration. At step S1314, these selected patterns are compared with the observed image or signal at the expected beam center by shifting up and down until a high correlation is obtained; otherwise the search continues (S1701) to find the bin with largest intensity value, A1 (S1708). At the same time, a computation of variations in bin intensities is performed as a function of "depth" of the A-mode-like, modified B-mode signal returned. If the bin with the highest intensity, A2, (S1708 and S1712) has value greater than the Noise+STD as one example, then an alert is displayed somewhere on or near the user's hand and a Report generated to be displayed there or elsewhere or in storage for later review; otherwise more detailed processing continues as before in FIG. 14. Note again that the threshold in step S1712 could be tightened to A2>Noise+M×STD if the system is reporting too many false positives, with some M>1. In other systems, it may be best to set the threshold at for example Noise+1.5 STD or other, to get less missed detections but more alarms. Thus, the threshold is a parameter that can be tuned to the particular user's preferences or a preference shared by a hospital or even a particular type of ward. As another example aiming to reduce false alarm rate further, the threshold can be applied to the first and second highest bin values, such that the alert (S1716) is not generated until both first and second bins are above threshold in step S1712.

From processing of the image in step S306/S606 an accumulating average is taken (S1702) over a number of frames, N, of the "total intensity," for each depth bin (S1704) which is the sum of red and blue intensities returned from each depth reachable by the Doppler beam; that is, within the Doppler window of the given ultrasonic instrument which is determined by its particular settings and computational limitations to keep up with the given frame rate. Thus, generating a one-dimensional array of bin values, a bin with the highest value is selected (S1708). If this value is greater than a fixed threshold such as the Noise+STD again (S1714 and S1712), then in one example, a further step (S1714) is to keep a "running average" of noise and its standard deviation of the noise from its average value. Noise is itself determined (S1714) in one example as a maximum absolute value, or in another example as a square-root(sum of squares(Bin value−average Bin value)). Thus, in this exemplary embodiment, steps S1708, S1712, S1714 and S1706 complete the noise determination of step S204.

In both FIGS. 12 and 17 in step S1214 and step S1714, respectively, there is a subtlety where the "Noise" is continually being estimated in "the running average." Noise and its standard deviation could be simultaneously updated by a Kalman Filter or some such recursive method as would be understood by one of ordinary skill in the art. In the first few recursions one will have to "seed" this filter so that it does not kick out these first few images. One way to do this is, for these initial iterations only, to force noise to be larger than the maximum A1 that occurred, so that the threshold is not exceeded until a "good" estimate of noise is obtained. If a frequency sweeping or stepping method is used as indicated in FIG. 17, then there will be one set of patterns for each frequency of vibration (the ultrasound frequency is generally a fixed value for a particular probe at a given depth, hence does not vary). If an array of bins of Doppler coloration is found to significantly overlap one of the key profiles in the patterns database, or if sweeping, significantly overlaps at a particular maximum, then an output is made to step S308 or S608.

Obviously, numerous modifications and variations of the present invention are possible in light of the above teachings. It is therefore to be understood that within the scope of the appended claims, the invention may be practiced otherwise than as specifically described herein.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, and to enable others of ordinary skill in the art to understand the embodiments disclosed herein.

INDUSTRIAL APPLICABILITY

Improved systems and methods for diagnosing an injury of a patient are provided herein. The system and methods provide for more accurate scans of the injury thereby enabling a combat medic, a medical technician, or even untrained individuals to quickly diagnose the injury. By providing more accurate information, the systems and methods provide the technician with additional information regarding treatment options, such as whether to transport the patient or treat the patient in place, potential for aspiration, and other information about dangerous fluid build-up such as size, depth, and types of surrounding tissues, thereby increasing survivability of the patient. The systems and methods can also provide a diagnosis of the injury as well as suggestions on actions to take to treat the patient.

The invention claimed is:

1. A method for diagnosing an injury, the method comprising:
   applying, from a single vibration device, one beam of vibration waves to an area near an injury to create a sloshing motion in any fluid within the area near the injury wherein the sloshing motion leads to greater movement than vibration waves inhomogeneous tissue located in that area;
   applying, from an ultrasound device, an ultrasound beam to an area of the injury;
   generating, via processing circuitry of the ultrasound device and based on signals created from reflections of the ultrasound beam generated by the ultrasound device, image data of the area of the injury reflects movement of any fluid relative to the homogeneous tissue;
   processing, via the processing circuitry, the image data;
   providing a diagnosis of the injury based on a result of the processing; and
   generating an alert when the diagnosis identifies an abnormality caused by the injury at the area of the injury, wherein the abnormality includes at least one of internal bleeding, hemothorax, pneumothorax, edema, exudate, or pericardial effusion, and
   wherein vibration waves produced by the vibration device cross with the ultrasound beam generated by the ultrasound device to lead to improved detection of any fluid within the area near the injury relative to an interface between the fluid and the homogeneous tissue.

2. The method of claim 1, wherein the vibration device includes only one transducer that is configured to be adjusted as a function of the image data.

3. The method of claim 2, wherein
   a transducer probe of the ultrasound device applies the ultrasound beam orthogonally to the area of the injury,
   the vibration device is applied on the skin at a lateral distance D from the transducer probe, and
   the distance D is a lateral distance which prevents interference generated by the vibration device until near the injury.

4. The method according to claim 3, wherein the vibration waves emitted by the vibration device are at a pulsatile constant frequency or frequency over a range.

5. The method according to claim 1, wherein
   the processing of the image data includes comparing one or more frames of the image data to one or more predetermined patterns, and
   the providing of the diagnosis and generating of the alert are based on the comparing.

6. The method according to claim 1, wherein the diagnosis is determined as a function of predetermined anatomy data of patients having the injury.

7. The method according to claim 1, wherein the alert includes a probability indicator indicating a probability of an internal injury based on the processing of the image data.

8. A system for diagnosing an injury, the system comprising:
   a single vibration device configured to apply one beam of vibration waves to an area near an injury to create a sloshing motion in any fluid within the area near the injury wherein the sloshing motion leads to greater movement than vibration waves in homogeneous tissue located in that area;
   an ultrasound device configured to apply an ultrasound beam to an area of the injury; and
   processing circuitry configured to:
      generate, based on signals from the ultrasound device generated from reflections of the ultrasound beam generated by the ultrasound device, image data of the area of the injury reflects movement of any fluid relative to the homogeneous tissue,
      process the image data,
      provide a diagnosis of the injury based on a result of the processing, and
      generate an alert when the diagnosis identifies an abnormality caused by the injury at the area of the injury, wherein the abnormality includes at least one of internal bleeding, hemothorax, pneumothorax, edema, exudate, or pericardial effusion; and
   wherein vibration waves produced by the single vibration device cross with the ultrasound beam at a point below a skin surface to lead to improved detection of any fluid within the area near the injury relative to an interface between the fluid and the homogeneous tissue.

9. The system of claim 8, wherein a vibration frequency output by the vibration device is adjusted as a function of the image data and the vibration device does not produce more than one vibration frequency at any time during use.

10. The system of claim 8, wherein
    a transducer probe of the ultrasound device is configured to apply the ultrasound beam orthogonally to the area of the injury,
    the vibration device is spaced at a lateral distance D from the transducer probe,
    the distance D is a lateral distance which prevents interference generated by the vibration waves emitted by the vibration device until near the point below the skin surface, and
    the distance D is within a range of 20 cm to 40 cm.

11. The system according to claim 8, wherein the vibration waves emitted by the vibration device is a pulsatile constant frequency or frequency over a range.

12. The system according to claim 8, wherein
the processing of the image data includes comparing one or more frames of the image data to one or more predetermined patterns, and
the providing of the diagnosis and generating of the alert are based on the comparing.

13. The system according to claim 8, wherein the diagnosis is determined as a function of predetermined anatomy data of patients having the injury.

14. The system according to claim 8, wherein the alert includes a probability indicator indicating a probability of an internal injury based on the processing of the image data.

15. The system according to claim 8, wherein during use, the ultrasound device and the vibration device are spaced from each other such that the vibration waves produced by the vibration device intersect at the area of injury with the ultrasound beam produced by the ultrasound device.

16. The system according to claim 8, wherein the ultrasound device is configured to operate at a frequency at least five times a frequency of the vibration device.

17. The method according to claim 1, wherein the ultrasound device is configured to operate at a frequency at least five times a frequency of the vibration device.

18. The method according to claim 1, wherein the vibration device emits vibration waves at one frequency that is capable of adjustment over time while the method is being performed; and
the vibration waves are emitted at an angle to the ultrasound beam.

\* \* \* \* \*